(12) United States Patent
Honigberg et al.

(10) Patent No.: US 7,825,118 B2
(45) Date of Patent: Nov. 2, 2010

(54) INHIBITORS OF BRUTON'S TYROSINE KINASE

(75) Inventors: Lee Honigberg, San Francisco, CA (US); Erik Verner, Belmont, CA (US); Zhengying Pan, Alpharetta, GA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 396 days.

(21) Appl. No.: 11/964,285

(22) Filed: Dec. 26, 2007

(65) Prior Publication Data

US 2008/0139582 A1 Jun. 12, 2008

Related U.S. Application Data

(63) Continuation-in-part of application No. 11/692,870, filed on Mar. 28, 2007, now Pat. No. 7,732,454, which is a continuation-in-part of application No. 11/617,645, filed on Dec. 28, 2006, now Pat. No. 7,514,444.

(60) Provisional application No. 60/828,590, filed on Oct. 6, 2006, provisional application No. 60/826,720, filed on Sep. 22, 2006.

(51) Int. Cl.
  *A01N 43/58* (2006.01)
  *A01N 43/60* (2006.01)
  *A61K 31/50* (2006.01)
  *A61K 31/495* (2006.01)
  *C07D 471/00* (2006.01)
  *C07D 487/00* (2006.01)
  *C07D 491/00* (2006.01)
  *C07D 495/00* (2006.01)
  *C07D 497/00* (2006.01)

(52) U.S. Cl. ...................... 514/249; 544/350
(58) Field of Classification Search ........................ None
See application file for complete search history.

(56) References Cited

U.S. PATENT DOCUMENTS

| 6,326,469 | B1 | 12/2001 | Ullrich et al. |
| 6,506,769 | B2 | 1/2003 | Snow et al. |
| 6,660,744 | B1 | 12/2003 | Hirst et al. |
| 6,753,348 | B2 | 6/2004 | Uckun et al. |
| 6,770,639 | B2 | 8/2004 | Snow et al. |
| 6,921,763 | B2 | 7/2005 | Hirst et al. |
| 2003/0040461 | A1 | 2/2003 | McAtee |
| 2003/0125235 | A1 | 7/2003 | Foxwell |
| 2004/0006083 | A1 | 1/2004 | Hirst et al. |
| 2005/0008640 | A1 | 1/2005 | Waegell et al. |
| 2005/0090499 | A1 | 4/2005 | Currie et al. |
| 2005/0101604 | A1 | 5/2005 | Currie et al. |
| 2005/0196851 | A1 | 9/2005 | Uckun |
| 2005/0209255 | A1 | 9/2005 | Jimenez et al. |
| 2006/0079494 | A1 | 4/2006 | Santi et al. |
| 2006/0167090 | A1 | 7/2006 | Uckun et al. |
| 2008/0076921 | A1 | 3/2008 | Honigberg et al. |
| 2008/0108636 | A1 | 5/2008 | Honigberg et al. |
| 2009/0181987 | A1 | 7/2009 | Honigberg |
| 2010/0004270 | A1 | 1/2010 | Honigberg |
| 2010/0022561 | A1 | 1/2010 | Honigberg |
| 2010/0041677 | A1 | 2/2010 | Honigberg |

FOREIGN PATENT DOCUMENTS

| WO | WO-97-28161 | 8/1997 |
| WO | WO-00-56737 A2 | 9/2000 |
| WO | WO-01-19829 A2 | 3/2001 |
| WO | WO-01-19829 A3 | 3/2001 |
| WO | WO-01-25238 A2 | 4/2001 |
| WO | WO-01-41754 | 6/2001 |
| WO | WO-01-44258 A1 | 6/2001 |
| WO | WO-02-38797 A2 | 5/2002 |
| WO | WO-02-080926 | 10/2002 |
| WO | WO-03-000187 | 1/2003 |
| WO | WO-2004-096253 | 11/2004 |
| WO | WO-2004-100868 A2 | 11/2004 |
| WO | WO-2004-100868 A3 | 11/2004 |
| WO | WO-2005-005429 | 1/2005 |
| WO | WO-2005-014599 | 2/2005 |
| WO | WO-2008-054827 A2 | 5/2008 |

OTHER PUBLICATIONS

Arnold, L.D. et al., "Pyrrolo[2,3-d]pyrimidines Containing an Extended 5-Substituent as Potent and Selective Inhibitors of lck 1," Bioorg. Med. Chem. Ltrs. 10:2167-2170 (2000).
Browning, J.L., "B cells move to centre stage: novel opportunities for autoimmune disease treatment", Nature Reviews/Drug Discovery vol. 5, Jul. 2006, pp. 564-576.
Burchat et al., "Pyrazolo[3,4-d]pyrimidines Containing an Extended 3-Substituent as Potent Inhibitors of Lck—a Selectivity Insight," Bioorg. Med. Chem. Ltrs. 12:1687-1690 (2002).
Cohen, M.S. et al., "Structural Bioinformatics-Based Design of Selective, Irreversible Kinase Inhibitors," Science, vol. 308, May 27, 2005, pp. 1318-1321.
Desiderio, S., "Role of Btk in B cell development and signaling," Curr. Op. in Immunology 1997, 9:534-540.
Fruman, D.A., "Xid-like Phenotypes: A B Cell Signalosome Takes Shape," Immunity 13:1-3 (Jul. 2000).
Gold, Michael R., "To make antibodies or not:signaling by the B-cell antigen receptor," Trends in Pharmacological Sciences, 23(7):316-324 (Jul. 2002).

(Continued)

*Primary Examiner*—James O Wilson
*Assistant Examiner*—Jeffrey H Murray
(74) *Attorney, Agent, or Firm*—Wilson Sonsini Goodrich & Rosati

(57) ABSTRACT

Disclosed herein are compounds that form covalent bonds with Bruton's tyrosine kinase (Btk). Also described are irreversible inhibitors of Btk. Methods for the preparation of the compounds are disclosed. Also disclosed are pharmaceutical compositions that include the compounds. Methods of using the Btk inhibitors are disclosed, alone or in combination with other therapeutic agents, for the treatment of autoimmune diseases or conditions, heteroimmune diseases or conditions, cancer, including lymphoma, and inflammatory diseases or conditions.

11 Claims, 7 Drawing Sheets

OTHER PUBLICATIONS

Horwood, Nicole J. et al., "Bruton's Tyrosin Kinase Is Required for Lipopolysaccharide—induced Tumor Necrosis Factor α Production," J. Exp. Med. 197(12):1603-1611 (Jun. 2003).

Iwaki, Shoki et al., "Btk Plays a Crucial Role in the Amplification of FceRI-mediated Mast Cell Activation by Kit," J. Biol. Chem. 280(48):40261-40270 (Dec. 2, 2005).

Jefferies, Caroline A. et al., "Bruton's Tyrosine Kinase Is a Toll/Interleukin-1 Receptor Domain-binding Protein That Participates in Nuclear Factor κB Activation by Toll-like Receptor 4," J. Biol. Chem. 278:26258-26264 (2003).

Kawakami, Yuko et al., "Terreic acid, a quinone epoxide inhibitor of Bruton's tyrosine kinase," PNAS USA 96:2227-2232 (1999).

Kuppers, R., "Mechanisms of B-cell lymphoma pathogenesis," Nature Reviews/Cancer, vol. 5, Apr. 2005, pp. 251-262.

Kurosaki, Tomohiro, "Functional dissection of BCR signaling pathways," Curr. Op. Imm. 12:276-281 (2000).

Mahajan, S. et al., "Rational Design and Synthesis of a Novel Antileukemic Agent Targeting Bruton's Tyrosine Kinase (BTK), LFM-A13 [α-Cyano-β-Methyl-N-(2,5-Dibromophenyl)Propenamide]," J. of Biol. Chem., vol. 274, No. 14, Apr. 2, 1999, pp. 9587-9599.

Mangla, Anita et al., "Pleiotropic consequences of Bruton tyrosin kinase deficiency in myeloid lineages lead to poor inflammatory responses," Blood 104(4):1191-1197 (2004).

Niiro, Hiroaki and Clark, Edward A., "Regulation of B-Cell Fate by Antigen-Receptor Signals," Nature Reviews 2:945-956 (2002).

Nisitani, S. et al., "In situ detection of activated Bruton's tyrosine kinase in the Ig signaling complex by phosphopeptide-specific monoclonal antibodies," PNAS USA 96:2221-2226 (1999).

Oligino, Thomas J. and Dalrymple, Stacie A., "Targeting B cells for the treatment of rheumatoid arthritis," Arthirits Res Ther 5(Suppl. 4):S7-S11 (2002).

Pan, Z. et al., "Discovery of Selectable Irreversible Inhibitors for Bruton's Tyrosine Kinase," ChemMedChem 2006, 1, 1-5.

Quek, L.S. et al., "A role for Bruton's tyrosine kinase (Btk) in platelet activation by collagen," Curr. Biol. 8(20):1137-1140 (1998).

Sada, Kiyonao and Yamamura, Hirohei, "Protein-Tyrosine Kinases and Adaptor Proteins in FceRI-Mediated Signaling in Mast Cells," Curr. Mol. Med. 3(1):85-94 (2003).

Schaeffer, Edward M. and Schwartzberg, Pamela L., "Tec family kinases in lymphocyte signaling and function," Curr. Op. Imm. 12:282-288 (2000).

Science IP CAS Search, Sep. 5, 2006.

Science IP CAS Search, Mar. 16, 2006.

Merged Markush Service Search, Jun. 27, 2005.

Shaffer, A.L. et al., Lymphoid malignancies: the dark side of B-cell differentiation, Nature Reviews/Immunology, vol. 2, Dec. 2002, pp. 920-932.

Smaill, J.B. et al., "Tyrosine Kinase Inhibitors. 15. 4-(Phenylamino)quinazoline and 4-(Phenylamino)prido[d] pyrimidine Acrylamides as Irresversible Inhibitors of the ATP Binding Site of the Epidermal Growth Factor Receptor," J. Med. Chem. 42(10):1803-1815 (1999).

Smith, C.I. Edvard et al., "The Tec family of cytoplasmic tyrosine kinases: mammalian Btk, Bmx, Itk, Tec, Txk and homologs in other species," BioEssays 23:436-446 (2001).

Smolen, Josef S. and Steiner, Gunter, "Therapeutic Strategies for Rheumatoid Arthritis," Nature Reviews 2:473-488 (2003).

Uckun, Fatih M. et al., "The Anti-leukemic Bruton's Tyrosin Kinase Inhibitor αcyano-β-hydroxy-β-mehyl-N-(2,5-dibromophenyl)Propenamide (LFM-A13)Prevents Fatal Thromboembolism," Leuk. Lymphoma 44(9):1569-1577 (2003).

Uckun, Fatih M. et al., "In Vivo Pharmacokinetic Features, Toxicity Profile, and Chemosensitizing Activity of α-Cyano-β-hydroxy-β-methyl-N-(2,5-dibromophenyl)propenamide (LFM-A13), a Novel Antileukemic Agent Targeting Bruton's Tyrosine Kinase," Clin. Cancer Res. 8:1224-1233 (2002).

Uckun, F.M., "Bruton's Tyrosin Kinase (BTK) as a Dual-Function Regulator of Apoptosis," Biochem. Pharmacology, vol. 56, pp. 683-691, 1998.

Uckun, Fatih M. et al., "BTK as a Mediator of Radiation-Induced Apoptosis in DT-40 Lymphoma B Cells,"Science vol. 273 No. 5278, pp. 1096-1100 (1996).

Vassilev, A.O. and Uckun, F.M., "Therapeutic Potential of Inhibiting Bruton's Tyrosine Kinase, (BTK)," Current Pharmaceutical Design, 2004, 10, 1757-1766.

Vassilev, Alexei et al., "Bruton's Tyrosine Kinase as an Inhibitor of the Fas/CD95 Death-inducing Signaling Complex," J. Biol. Chem. 274(3):1646-1656 (1999).

Yamamoto, Noriyuki et al., "The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents," J. Pharma. And Exp. Therapeutics 306(3):1174-1181 (2003).

Luskova, P. and Draber, P., "Modulation of the Fce Receptor I Signaling by Tyrosin Kinase Inhibitors: Search for Therapeutic Targets of Inflammatory and Allergy Diseases," Curr. Pharmaceutical Design 10:1727-1737 (2004).

PCT/US06/49626 Search Report dated Apr. 9, 2008.

Vippagunta et al., "Crystalline Solids," Advanced Drug Delivery Reviews 48:3-26 (2001).

Dorwald, F. A. *Side Reactions in Organic Synthesis*, Wiley:VCH, Weinheim pg. IX of Preface, Wiley-VCH Verlag GmbH & Co. KGaA (2005).

EP06850039 Supplemental Search Report dated Feb. 9, 2010.

| # | 473 | 474 | 475 | 476 | 477 | 478 | 479 | 480 | 481 | 482 | 483 |
|---|---|---|---|---|---|---|---|---|---|---|---|
| BTK | I | T | E | Y | M | A | N | G | C | L | L |
| BMX | V | T | E | Y | M | A | R | G | C | L | L |
| TEC | V | T | E | F | M | E | R | G | C | L | L |
| TXK | V | T | E | F | M | E | N | G | C | L | L |
| ITK | V | F | E | F | M | E | H | G | C | L | S |
| EGFR | I | T | Q | L | M | P | F | G | C | L | L |
| ErbB2 | V | T | Q | L | M | P | Y | G | C | L | L |
| ErbB4 | V | T | Q | L | M | P | H | G | C | L | L |
| JAK3 | V | M | E | Y | L | P | S | G | C | L | R |
| BLK | V | T | E | Y | L | P | S | G | C | L | L |
| LCK | I | T | E | Y | M | E | N | G | C | L | V |
| LYN | I | T | E | Y | M | A | K | G | S | L | L |
| SYK | V | M | E | M | A | E | L | G | P | L | N |

Fig. 1

INHIBITORS OF BRUTON'S TYROSINE KINASE

RELATED APPLICATIONS

This application is a continuation-in-part patent application of U.S. patent application Ser. No. 11/692,870 filed Mar. 28, 2007 which is a continuation-in-part of U.S. patent application Ser. No. 11/617,645 filed Dec. 28, 2006, the latter two of which claim the benefit of U.S. Provisional Patent Application No. 60/826,720, filed Sep. 22, 2006 and U.S. Provisional Patent Application No. 60/828,590 filed Oct. 6, 2006; all of which are herein incorporated by reference.

FIELD OF THE INVENTION

Described herein are compounds, methods of making such compounds, pharmaceutical compositions and medicaments containing such compounds, and methods of using such compounds and compositions to inhibit the activity of tyrosine kinases.

BACKGROUND OF THE INVENTION

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival (Kurosaki, *Curr Op Imm*, 2000, 276-281; Schaeffer and Schwartzberg, *Curr Op Imm* 2000, 282-288). In addition, Btk plays a role in a number of other hematopoetic cell signaling pathways, e.g., Toll like receptor (TLR) and cytokine receptor mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See, e.g., C. A. Jeffries, et al., (2003), *Journal of Biological Chemistry* 278:26258-26264; N. J. Horwood, et al., (2003), *The Journal of Experimental Medicine* 197:1603-1611; Iwaki et al. (2005), *Journal of Biological Chemistry* 280(48):40261-40270; Vassilev et al. (1999), *Journal of Biological Chemistry* 274(3):1646-1656, and Quek et al. (1998), *Current Biology* 8(20):1137-1140.

SUMMARY OF THE INVENTION

Described herein are inhibitors of Bruton's tyrosine kinase (Btk). Also described herein are irreversible inhibitors of Btk. Further described are irreversible inhibitors of Btk that form a covalent bond with a cysteine residue on Btk. Further described herein are irreversible inhibitors of other tyrosine kinases, wherein the other tyrosine kinases share homology with Btk by having a cysteine residue (including a Cys 481 residue) that can form a covalent bond with the irreversible inhibitor (such tyrosine kinases, are referred herein as "Btk tyrosine kinase cysteine homologs"). Also described herein are methods for synthesizing such irreversible inhibitors, methods for using such irreversible inhibitors in the treatment of diseases (including diseases wherein irreversible inhibition of Btk provides therapeutic benefit to a patient having the disease). Further described are pharmaceutical formulations that include an irreversible inhibitor of Btk.

Compounds described herein include those that have a structure of any of Formula (A1-A6), Formula (B1-B6), Formula (C1-C6), or Formula (D1-D6), and pharmaceutically acceptable salts, solvates, esters, acids and prodrugs thereof. In certain embodiments, isomers and chemically protected forms of compounds having a structure represented by any of Formula (A1-A6), Formula (B1-B6), Formula (C1-C6), or Formula (D1-D6), are also provided.

In one aspect, provided herein are compounds of Formula (D1-D6). Formula (D1-D6) are as follows:

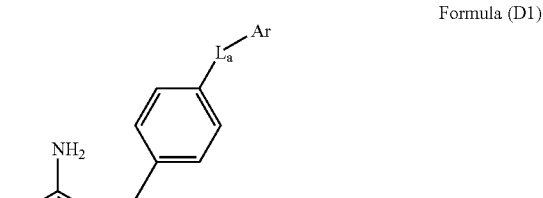

Formula (D1)

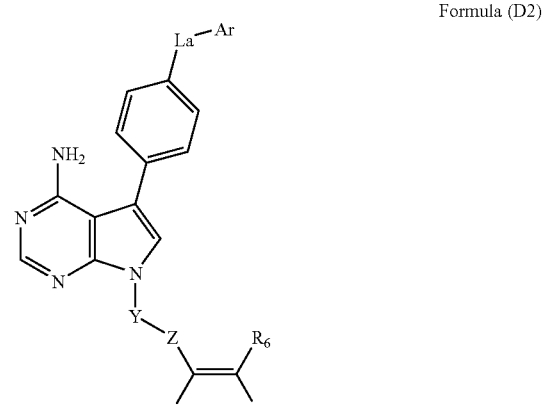

Formula (D2)

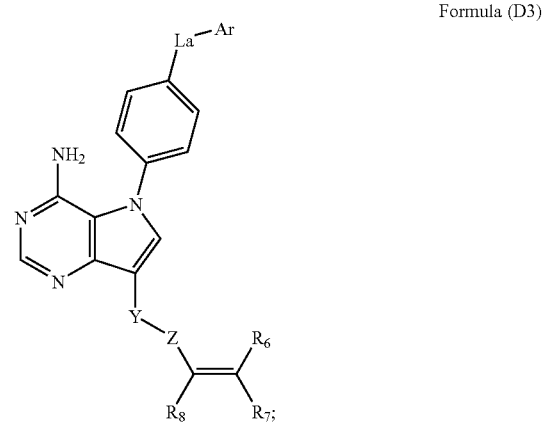

Formula (D3)

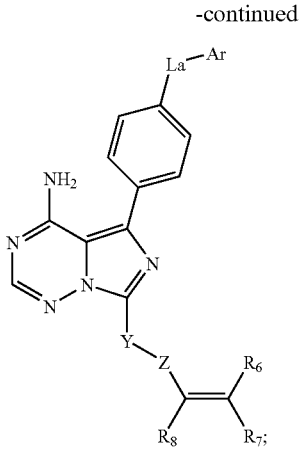

Formula (D4)

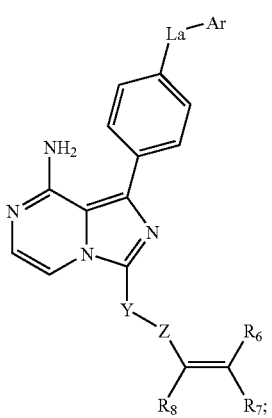

Formula (D5)

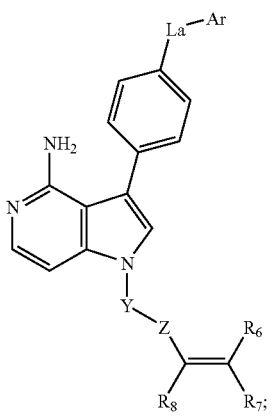

Formula (D6)

wherein:

$L_a$ is $CH_2$, O, NH or S;

Ar is a substituted or unsubstituted aryl, or a substituted or unsubstituted heteroaryl;

Y is an optionally substituted group selected from among alkyl, heteroalkyl, cycloalkyl, heterocycloalkyl, aryl, and heteroaryl;

Z is C(=O), OC(=O), NHC(=O), C(=S), S(=O)$_x$, OS(=O)$_x$, NHS(=O)$_x$, where x is 1 or 2;

$R_7$ and $R_8$ are independently selected from among H, unsubstituted $C_1$-$C_4$alkyl, substituted $C_1$-$C_4$alkyl, unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or $R_7$ and $R_8$ taken together form a bond;

$R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl); and pharmaceutically active metabolites, or pharmaceutically acceptable solvates, pharmaceutically acceptable salts, or pharmaceutically acceptable prodrugs thereof.

For any and all of the embodiments, substituents can be selected from among from a subset of the listed alternatives. For example, in some embodiments, $L_a$ is $CH_2$, O, or NH. In other embodiments, $L_a$ is O or NH. In yet other embodiments, $L_a$ is O.

In some embodiments, Ar is a substituted or unsubstituted aryl. In yet other embodiments, Ar is a 6-membered aryl. In some other embodiments, Ar is phenyl.

In some embodiments, x is 2. In yet other embodiments, Z is C(=O), OC(=O), NHC(=O), S(=O)$_x$, OS(=O)$_x$, or NHS(=O)$_x$. In some other embodiments, Z is C(=O), NHC(=O), or S(=O)$_2$.

In some embodiments, $R_7$ and $R_8$ are independently selected from among H, unsubstituted $C_1$-$C_4$ alkyl, substituted $C_1$-$C_4$alkyl, unsubstituted $C_1$-$C_4$heteroalkyl, and substituted $C_1$-$C_4$heteroalkyl; or $R_7$ and $R_8$ taken together form a bond. In yet other embodiments, each of $R_7$ and $R_8$ is H; or $R_7$ and $R_8$ taken together form a bond.

In some embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted aryl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In some other embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-N($C_1$-$C_3$alkyl)$_2$, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In yet other embodiments, $R_6$ is H, substituted or unsubstituted $C_1$-$C_4$alkyl, —$CH_2$—O—($C_1$-$C_3$alkyl), —$CH_2$—N($C_1$-$C_3$alkyl)$_2$, $C_1$-$C_4$alkyl(phenyl), or $C_1$-$C_4$alkyl(5- or 6-membered heteroaryl). In yet other embodiments, $R_6$ is H, substituted or unsubstituted $C_1$-$C_4$alkyl, —$CH_2$—O—($C_1$-$C_3$alkyl), —$CH_2$—($C_1$-$C_6$alkylamino), $C_1$-$C_4$alkyl(phenyl), or $C_1$-$C_4$alkyl(5- or 6-membered heteroaryl). In some embodiments, $R_6$ is H, substituted or unsubstituted $C_1$-$C_4$alkyl, —$CH_2$—O—($C_1$-$C_3$alkyl), —$CH_2$—N($C_1$-$C_3$alkyl)$_2$, $C_1$-$C_4$alkyl(phenyl), or $C_1$-$C_4$alkyl (5- or 6-membered heteroaryl containing 1 or 2 N atoms), or $C_1$-$C_4$alkyl(5- or 6-membered heterocycloalkyl containing 1 or 2 N atoms).

In some embodiments, Y is an optionally substituted group selected from among alkyl, heteroalkyl, cycloalkyl, and heterocycloalkyl. In other embodiments, Y is an optionally substituted group selected from among $C_1$-$C_6$alkyl, $C_1$-$C_6$heteroalkyl, 4-, 5-, 6-, or 7-membered cycloalkyl, and 4-, 5-, 6-, or 7-membered heterocycloalkyl. In yet other embodiments, Y is an optionally substituted group selected from among $C_1$-$C_6$alkyl, $C_1$-$C_6$heteroalkyl, 5- or 6-membered cycloalkyl, and 5- or 6-membered heterocycloalkyl containing 1 or 2 N atoms. In some other embodiments, Y is a 5- or 6-membered cycloalkyl, or a 5- or 6-membered heterocycloalkyl containing 1 or 2 N atoms. In some embodiments, Y is a 4-, 5-, 6-, or 7-membered cycloalkyl ring; or Y is a 4-, 5-, 6-, or 7-membered heterocycloalkyl ring.

Any combination of the groups described above for the various variables is contemplated herein.

In one aspect, provided herein is a compound selected from among:

1-(3-(4-amino-3-(4-phenoxyphenyl)-1H-pyrazolo[3,4-d]pyrimidin-1-yl)piperidin-1-yl)prop-2-en-1-one (Compound 4); (E)-1-(3-(4-amino-3-(4-phenoxyphenyl)-1H-pyrazolo[3,4-d]pyrimidin-1-yl)piperidin-1-yl)but-2-en-1-one (Compound 5); 1-(3-(4-amino-3-(4-phenoxyphenyl)-1H-pyrazolo[3,4-d]pyrimidin-1-yl)piperidin-1-yl)sulfonylethene (Compound 6); 1-(3-(4-amino-3-(4-phenoxyphenyl)-1H-pyrazolo[3,4-d]pyrimidin-1-yl)piperidin-1-yl)prop-2-yn-1-one (Compound 8); 1-(4-(4-amino-3-(4-phenoxyphenyl)-1H-pyrazolo[3,4-d]pyrimidin-1-yl)piperidin-1-yl)prop-2-en-1-one (Compound 9); N-((1s,4s)-4-(4-amino-3-(4-phenoxyphenyl)-1H-pyrazolo[3,4-d]pyrimidin-1-yl)cyclohexyl)acrylamide (Compound 10); 1-((R)-3-(4-amino-3-(4-phenoxyphenyl)-1H-pyrazolo[3,4-d]pyrimidin-1-yl)pyrrolidin-1-yl)prop-2-en-1-one (Compound II); 1-((S)-3-(4-amino-3-(4-phenoxyphenyl)-1H-pyrazolo[3,4-d]pyrimidin-1-yl)pyrrolidin-1-yl)prop-2-en-1-one (Compound 12); 1-((R)-3-(4-amino-3-(4-phenoxyphenyl)-1H-pyrazolo[3,4-d]pyrimidin-1-yl)piperidin-1-yl)prop-2-en-1-one (Compound 13); 1-((S)-3-(4-amino-3-(4-phenoxyphenyl)-1H-pyrazolo[3,4-d]pyrimidin-1-yl)piperidin-1-yl)prop-2-en-1-one (Compound 14); and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one (Compound 15).

In a further aspect are provided pharmaceutical compositions, which include a therapeutically effective amount of at least one of any of the compounds herein, or a pharmaceutically acceptable salt, pharmaceutically active metabolite, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

In certain embodiments, provided herein is a pharmaceutical composition containing: i) a physiologically acceptable carrier, diluent, and/or excipient; and ii) one or more compounds provided herein.

In one aspect, provided herein are methods for treating a patient by administering a compound provided herein. In some embodiments, provided herein is a method of inhibiting the activity of tyrosine kinase(s), such as Btk, or of treating a disease, disorder, or condition, which would benefit from inhibition of tyrosine kinase(s), such as Btk, in a patient, which includes administering to the patient a therapeutically effective amount of at least one of any of the compounds herein, or pharmaceutically acceptable salt, pharmaceutically active metabolite, pharmaceutically acceptable prodrug, or pharmaceutically acceptable solvate.

In another aspect, provided herein is the use of a compound disclosed herein for inhibiting Bruton's tyrosine kinase (Btk) activity or for the treatment of a disease, disorder, or condition, which would benefit from inhibition of Bruton's tyrosine kinase (Btk) activity.

In some embodiments, compounds provided herein are administered to a human. In some embodiments, compounds provided herein are orally administered.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (Btk) activity.

Articles of manufacture including packaging material, a compound or composition or pharmaceutically acceptable derivative thereof provided herein, which is effective for inhibiting the activity of tyrosine kinase(s), such as Btk, within the packaging material, and a label that indicates that the compound or composition, or pharmaceutically acceptable salt, pharmaceutically active metabolite, pharmaceutically acceptable prod rug, or pharmaceutically acceptable solvate thereof, is used for inhibiting the activity of tyrosine kinase(s), such as Btk, are provided.

In another aspect are inhibited tyrosine kinases comprising a Bruton's tyrosine kinase, a Bruton's tyrosine kinase homolog, or a Btk tyrosine kinase cysteine homolog thereof covalently bound to an inhibitor having the structures:

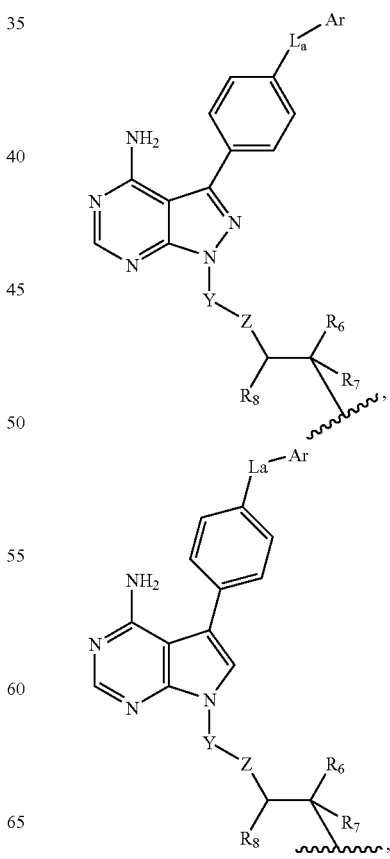

-continued

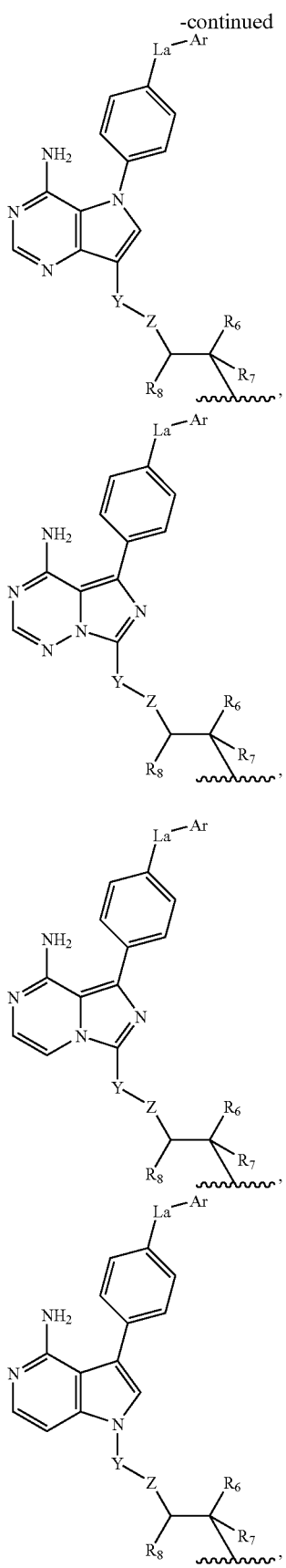

wherein

~~~

5 indicates the point of attachment between the inhibitor and the tyrosine kinase. In a further embodiment, the inhibitor is covalently bound to a cysteine residue on the tyrosine kinase.

In a further aspect, provided herein is a method for inhibiting Bruton's tyrosine kinase in a subject in need thereof by administering to the subject thereof a composition containing a therapeutically effective amount of at least one compound having the structure of any of Formula (A1-A6), Formula (B1-B6), Formula (C1-C6), or Formula (D1-D6). In some embodiments, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In other embodiments, the subject in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In certain embodiments, the subject in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In further embodiments, the subject in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of at least one compound having the structure of any of Formula (A1-A6), Formula (B1-B6), Formula (C1-C6), or Formula (D1-D6). In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In a further aspect, provided herein is a method for treating a heteroimmune condition or disease by administering to a subject in need thereof a composition containing a therapeutically effective amount of at least one compound having the structure of any of Formula (A1-A6), Formula (B1-B6), Formula (C1-C6), or Formula (D1-D6). In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound having the structure of any of Formula (A1-A6), Formula (B1-B6), Formula (C1-C6), or Formula (D1-D6). In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound having the structure of any of Formula (A1-A6), Formula (B1-B6), Formula (C1-C6), or Formula (D1-D6). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of any of Formula (A1-A6), Formula (B1-B6), Formula (C1-C6), or Formula (D1-D6). In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating a heteroimmune condition or disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating an inflammatory disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase. In yet another aspect, provided herein is a method for treating a cancer by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase. In another aspect, provided herein is a method for treating a thromboembolic disorder by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In another aspect are methods for modulating, including irreversibly inhibiting the activity of Btk or other tyrosine kinases, wherein the other tyrosine kinases share homology with Btk by having a cysteine residue (including a Cys 481 residue) that can form a covalent bond with at least one irreversible inhibitor described herein, in a mammal comprising administering to the mammal at least once an effective amount of at least one compound having the structure of any of Formula (A1-A6), Formula (B1-B6), Formula (C1-C6), or Formula (D1-D6). In another aspect are methods for modulating, including irreversibly inhibiting, the activity of Btk in a mammal comprising administering to the mammal at least once an effective amount of at least one compound having the structure of any of Formula (A1-A6), Formula (B1-B6), Formula (C1-C6), or Formula (D1-D6). In another aspect are methods for treating Btk-dependent or Btk mediated conditions or diseases, comprising administering to the mammal at least once an effective amount of at least one compound having the structure of any of Formula (A1-A6), Formula (B1-B6), Formula (C1-C6), or Formula (D1-D6).

In another aspect are methods for treating inflammation comprising administering to the mammal at least once an effective amount of at least one compound having the structure of Formula (A1-A6), (B1-B6), (C1-C6), or (D1-D6).

A further aspect are methods for the treatment of cancer comprising administering to the mammal at least once an effective amount of at least one compound having the structure of Formula (A1-A6), (B1-B6), (C1-C6), or (D1-D6). The type of cancer includes, but is not limited to, pancreatic cancer and other solid or hematological tumors.

In another aspect are methods for treating respiratory diseases comprising administering to the mammal at least once an effective amount of at least one compound having the structure of Formula (A1-A6), (B1-B6), (C1-C6), or (D1-D6). In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, In another aspect are methods for preventing rheumatoid arthritis and osteoarthritis comprising administering to the mammal at least once an effective amount of at least one compound having the structure of Formula (A1-A6), (B1-B6), (C1-C6), or (D1-D6).

In another aspect are methods for treating inflammatory responses of the skin comprising administering to the mammal at least once an effective amount of at least one compound having the structure of Formula (A1-A6), (B1-B6), (C1-C6), or (D1-D6). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a first compound having the structure of Formula (A1-A6), (B1-B6), (C1-C6), or (D1-D6).

In another aspect is the use of a compound of Formula (A1-A6), (B1-B6), (C1-C6), or (D1-D6) in the manufacture of a medicament for treating an inflammatory disease or condition in an animal in which the activity of Btk or other tyrosine kinases, wherein the other tyrosine kinases share homology with Btk by having a cysteine residue (including a Cys 481 residue) that can form a covalent bond with at least one irreversible inhibitor described herein, contributes to the pathology and/or symptoms of the disease or condition. In one embodiment of this aspect, the tyrosine kinase protein is Btk. In another or further embodiment of this aspect, the inflammatory disease or conditions are respiratory, cardiovascular, or proliferative diseases.

In any of the aforementioned aspects are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (i) the effective amount of the compound is administered rectally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned aspects involving the treatment of proliferative disorders, including cancer, are further embodiments comprising administering at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzamab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned aspects involving the prevention or treatment of Btk-dependent or tyrosine kinase mediated diseases or conditions are further embodiments comprising identifying patients by screening for a tyrosine kinase gene haplotype. In further or alternative embodiments the tyrosine kinase gene haplotype is a tyrosine kinase pathway gene, while in still further or alternative embodiments, the tyrosine kinase gene haplotype is a Btk haplotype.

Also described herein are methods to identify biomarkers for patient selection or patient monitoring prior to or during treatment with the compound of Formula (A1-A6), (B1-B6), (C1-C6) or (D1-D6). In one embodiment, a patient that has lymphoma is administered a pharmaceutical composition of the compound of Formula (A1-A6), (B1-B6), (C1-C6) or (D1-D6) which inhibits B cell receptor (BCR) signaling. In another embodiment, the inhibition of the BCR signaling by a compound of Formula (A1-A6), (B1-B6), (C1-C6) or (D1-D6) is correlated with the induction of apoptosis. In another embodiment, a patient with lymphoma is selected for treatment with a compound of Formula (A1-A6), (B1-B6), (C1-C6) or (D1-D6) based on a biomarker that indicates that the lymphoma in that patient has high levels of pErk or Erk transcriptional targets. In another embodiment, the response to treatment with a compound of Formula (A1-A6), (B1-B6), (C1-C6) or (D1-D6) is measured by a reduction in levels of pErk or Erk transcriptional targets.

In a further or alternative embodiment, the compound of Formula (A1-A6), (B1-B6), (C1-C6) or (D1-D6) are irreversible inhibitors of Bruton's tyrosine kinase (Btk), while in still further or alternative embodiments, such irreversible inhibitors are selective for Btk. In even further or alternative embodiments, such inhibitors have an $IC_{50}$ below 10 microM in enzyme assay. In one embodiment, a Btk irreversible inhibitor has an $IC_{50}$ of less than 1 microM, and in another embodiment, less than 0.25 microM.

In further or alternative embodiment, the compound of Formula (A1-A6), (B1-B6), (C1-C6) or (D1-D6) are selective irreversible inhibitors for Btk over Itk. In further or alternative embodiment, the compound of Formula (A1-A6), (B1-B6), (C1-C6) or (D1-D6) are selective irreversible inhibitors for Btk over Lck. In further or alternative embodiment, the compound of Formula (A1-A6), (B1-B6), (C1-C6) or (D1-D6) are selective irreversible inhibitors for Btk over ABL. In further or alternative embodiment, the compound of Formula (A1-A6), (B1-B6), (C1-C6) or (D1-D6) are selective irreversible inhibitors for Btk over CMET. In further or alternative embodiment, the compound of Formula (A1-A6), (B1-B6), (C1-C6) or (D1-D6) are selective irreversible inhibitors for Btk over EGFR. In further or alternative embodiment, the compound of Formula (A1-A6), (B1-B6), (C1-C6) or (D1-D6) are selective irreversible inhibitors for Btk over Lyn. In further or alternative embodiment, the compound of Formula (A1-A6), (B1-B6), (C1-C6) or (D1-D6) are selective irreversible inhibitors for Btk over Bmx. In further or alternative embodiment, the compound of Formula (A1-A6), (B1-B6), (C1-C6) or (D1-D6) are selective irreversible inhibitors for Btk over JAK3. In further or alternative embodiment, the compound of Formula (A1-A6), (B1-B6), (C1-C6) or (D1-D6) are selective irreversible inhibitors for Btk over Blk. In further or alternative embodiment, the compound of Formula (A1-A6), (B1-B6), (C1-C6) or (D1-D6) are selective irreversible inhibitors for Btk over Syk.

In further or alternative embodiments, the irreversible Btk inhibitors are also inhibitors of EGFR.

Other objects, features and advantages of the methods and compositions described herein will become apparent from the following detailed description. It should be understood, however, that the detailed description and the specific examples, while indicating specific embodiments, are given by way of illustration only. The section headings used herein are for organizational purposes only and are not to be construed as limiting the subject matter described.

Certain Terminology

Unless defined otherwise, all technical and scientific terms used herein have the same meaning as is commonly understood by one of skill in the art to which the claimed subject matter belongs. In the event that there are a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group can be a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups can be substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

As used herein, the term "non-cyclic alkyl" refers to an alkyl that is not cyclic (i.e., a straight or branched chain containing at least one carbon atom). Non-cyclic alkyls can be fully saturated or can contain non-cyclic alkenes and/or alkynes. Non-cyclic alkyls can be optionally substituted.

The term "alkenyl" refers to a type of alkyl group in which the first two atoms of the alkyl group form a double bond that is not part of an aromatic group. That is, an alkenyl group begins with the atoms —C(R)═C(R)—R, wherein R refers to the remaining portions of the alkenyl group, which are either the same or different. The alkenyl moiety is optionally branched, straight chain, or cyclic (in which case, it would also be known as a "cycloalkenyl" group). Depending on the structure, an alkenyl group can be a monoradical or a diradical (i.e., an alkenylene group). Alkenyl groups can be optionally substituted. Non-limiting examples of an alkenyl group include —CH═CH$_2$, —C(CH$_3$)═CH$_2$, —CH═CHCH$_3$, C(CH$_3$)═CHCH$_3$. Alkenylene groups include, but are not limited to, —CH═CH—, —C(CH$_3$)═CH—, —CH═CHCH$_2$—, —CH═CHCH$_2$CH$_2$— and —C(CH$_3$)═CHCH$_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group can be a monoradical or a diradical (i.e., an alkynylene group). Alkynyl groups can be optionally substituted. Non-limiting examples of an alkynyl group include, but are not limited to, —C≡CH, —C≡CCH$_3$, —CγCCH$_2$CH$_3$, —C≡C—, and —C≡CCH$_2$. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are found in sources such as Greene and Wuts, Protective Groups in Organic Synthesis, 3$^{rd}$ Ed., John Wiley & Sons, New York, N.Y., 1999, which is incorporated herein by reference for this disclosure.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized n-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

"Aralkyl" means an alkyl radical, as defined herein, substituted with an aryl group. Non-limiting aralkyl groups include, benzyl, phenethyl, and the like.

"Aralkenyl" means an alkenyl radical, as defined herein, substituted with an aryl group, as defined herein.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

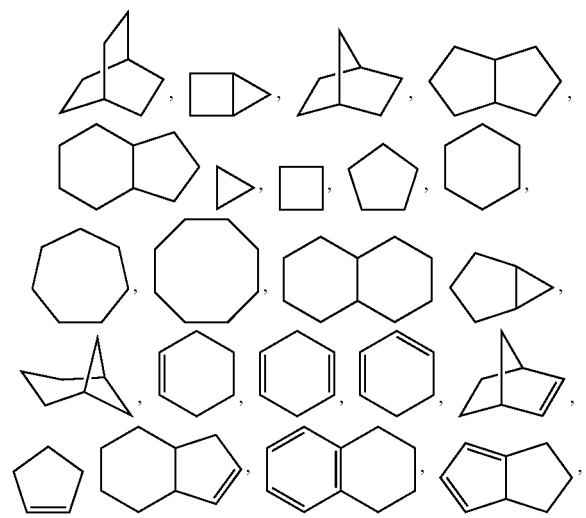

and the like. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

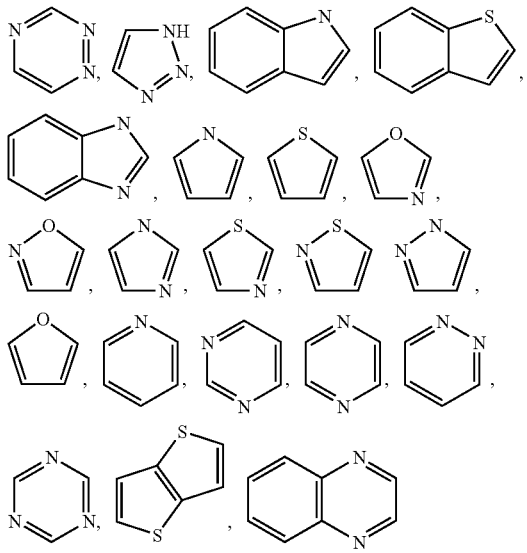

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

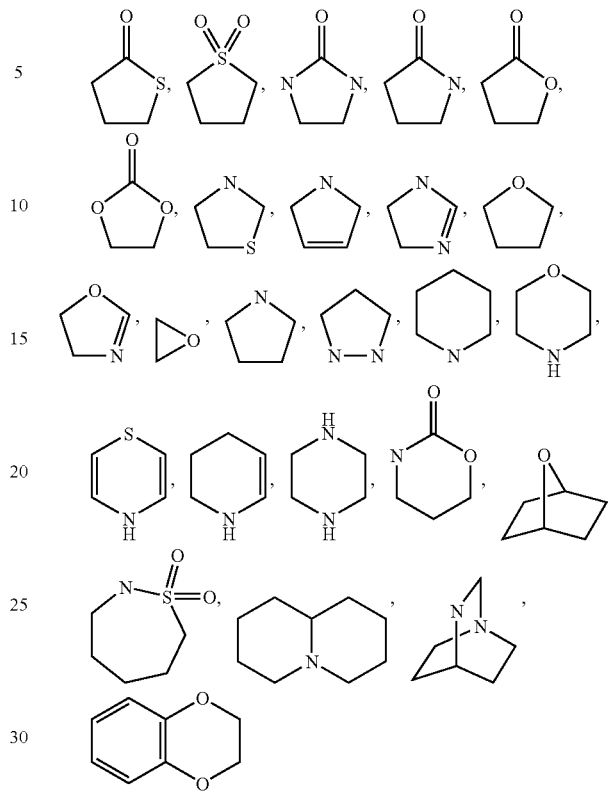

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —$CF_3$, $CH_2CF_3$, $CF_2CF_3$, $CH_2CH_2CF_3$ and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—

CH₂—N(CH₃)—CH₃, —CH₂—S—CH₂—CH₃, —CH₂—CH₂—S(O)—CH₃, —CH₂—CH₂—S(O)₂—CH₃, —CH=CH—O—CH₃, —Si(CH₃)₃, —CH₂—CH=N—OCH₃, and CH=CH—N(CH₃)—CH₃. In addition, up to two heteroatoms may be consecutive, such as, by way of example, —CH₂—NH—OCH₃ and CH₂—O—Si(CH₃)₃.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

An "isocyanato" group refers to a —NCO group.

An "isothiocyanato" group refers to a —NCS group.

The term "moiety" refers to a specific segment or functional group of a molecule. Chemical moieties are often recognized chemical entities embedded in or appended to a molecule.

A "sulfinyl" group refers to a —S(=O)—R.

A "sulfonyl" group refers to a —S(=O)₂—R.

A "thioalkoxy" or "alkylthio" group refers to a S-alkyl group.

A "alkylthioalkyl" group refers to an alkyl group substituted with a S-alkyl group.

As used herein, the term "O-carboxy" or "acyloxy" refers to a group of formula RC(=O)O—.

"Carboxy" means a —C(O)OH radical.

As used herein, the term "acetyl" refers to a group of formula —C(=O)CH₃.

"Acyl" refers to the group —C(O)R.

As used herein, the term "trihalomethanesulfonyl" refers to a group of formula X₃CS(=O)₂— where X is a halogen.

As used herein, the term "cyano" refers to a group of formula —CN.

"Cyanoalkyl" means an alkyl radical, as defined herein, substituted with at least one cyano group.

As used herein, the term "N-sulfonamido" or "sulfonylamino" refers to a group of formula RS(=O)₂NH—.

As used herein, the term "O-carbamyl" refers to a group of formula —OC(=O)NR₂.

As used herein, the term "N-carbamyl" refers to a group of formula ROC(=O)NH—.

As used herein, the term "O-thiocarbamyl" refers to a group of formula —OC(=S)NR₂.

As used herein, the term "N-thiocarbamyl" refers to a group of formula ROC(=S)NH—.

As used herein, the term "C-amido" refers to a group of formula —C(=O)NR₂.

"Aminocarbonyl" refers to a —CONH₂ radical.

As used herein, the term "N-amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be L$_s$R$_s$, wherein each L$_s$ is independently selected from a bond, —O—, —C(=O)—, —S—, —S(=O)—, —S(=O)₂—, —NH—, —NHC(O)—, —C(O)NH—, S(=O)₂NH—, —NHS(=O)₂, —OC(O)NH—, —NHC(O)O—, -(substituted or unsubstituted C₁-C₆ alkyl), or -(substituted or unsubstituted C₂-C₆ alkenyl); and each R$_s$ is independently selected from H, (substituted or unsubstituted C₁-C₄alkyl), (substituted or unsubstituted C₃-C₆cycloalkyl), heteroaryl, or heteroalkyl. The protecting groups that may form the protective derivatives of the above substituents are found in sources such as Greene and Wuts, above.

The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile. The "G" groups presented in any of Formula (A1-A6), Formula (B1-B6), Formula (C1-C6), or Formula (D1-D6) are non-limiting examples of Michael acceptor moieties.

The term "nucleophile" or "nucleophilic" refers to an electron rich compound, or moiety thereof. An example of a nucleophile includes, but in no way is limited to, a cysteine residue of a molecule, such as, for example Cys 481 of Btk.

The term "electrophile", or "electrophilic" refers to an electron poor or electron deficient molecule, or moiety thereof. Examples of electrophiles include, but in no way are limited to, Micheal acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (A1-A6), Formula (B1-B6), Formula (C1-C6), or Formula (D1-D6), dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which compounds disclosed herein, such as, compounds of any of Formula (A1-A6), Formula (B1-B6), Formula (C1-C6), or Formula (D1-D6), are absorbed into the general circulation when the pharmaceutical composition is taken orally as compared to intravenous injection.

"Blood plasma concentration" refers to the concentration of compounds disclosed herein, such as, compounds of any of Formula (A1-A6), Formula (B1-B6), Formula (C1-C6), or Formula (D1-D6), in the plasma component of blood of a subject. It is understood that the plasma concentration of compounds of any of Formula (A1-A6), Formula (B1-B6), Formula (C1-C6), or Formula (D1-D6), may vary significantly between subjects, due to variability with respect to metabolism and/or possible interactions with other therapeutic agents. In accordance with one embodiment disclosed herein, the blood plasma concentration of the compounds of any of Formula (A1-A6), Formula (B1-B6), Formula (C1-C6), or Formula (D1-D6), may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of any of Formula (A1-A6), Formula (B1-B6), Formula (C1-C6), or Formula (D1-D6), may vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Acession No. AAB47246), dog (GenBank Acession No. XP_549139), rat (GenBank Acession No. NP_001007799), chicken (GenBank Acession No. NP_989564), or zebra fish (GenBank Acession No. XP_698117), and fusion proteins of any of the foregoing that exhibit kinase activity towards one or more substrates of Bruton's tyrosine kinase (e.g. a peptide substrate having the amino acid sequence "AVLESEEELYSSARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (A1-A6), Formula (B1-B6), Formula (C1-C6), or Formula (D1-D6), age, weight, general condition of the subject, the condition being treated, the severity of the condition being treated, and the judgment of the prescribing physician.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. Other examples of kinases having homologous cysteines are shown in FIG. 1. See also the sequence alignments of tyrosine kinases (TK) published on the world wide web at kinase.com/human/kinome/phylogeny.html.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase, as shown in FIG. 1.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "pERK" refers to phosphorylated ERK1 and ERK2 at Thr202/Tyr 204 as detected by commercially available phospho-specific antibodies (e.g. Cell Signaling Technologies #4377).

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

BRIEF DESCRIPTION OF THE FIGURES

FIG. 1 presents a sequence comparison of Btk with other tyrosine kinases.

DETAILED DESCRIPTION OF THE INVENTION

Figure 2:
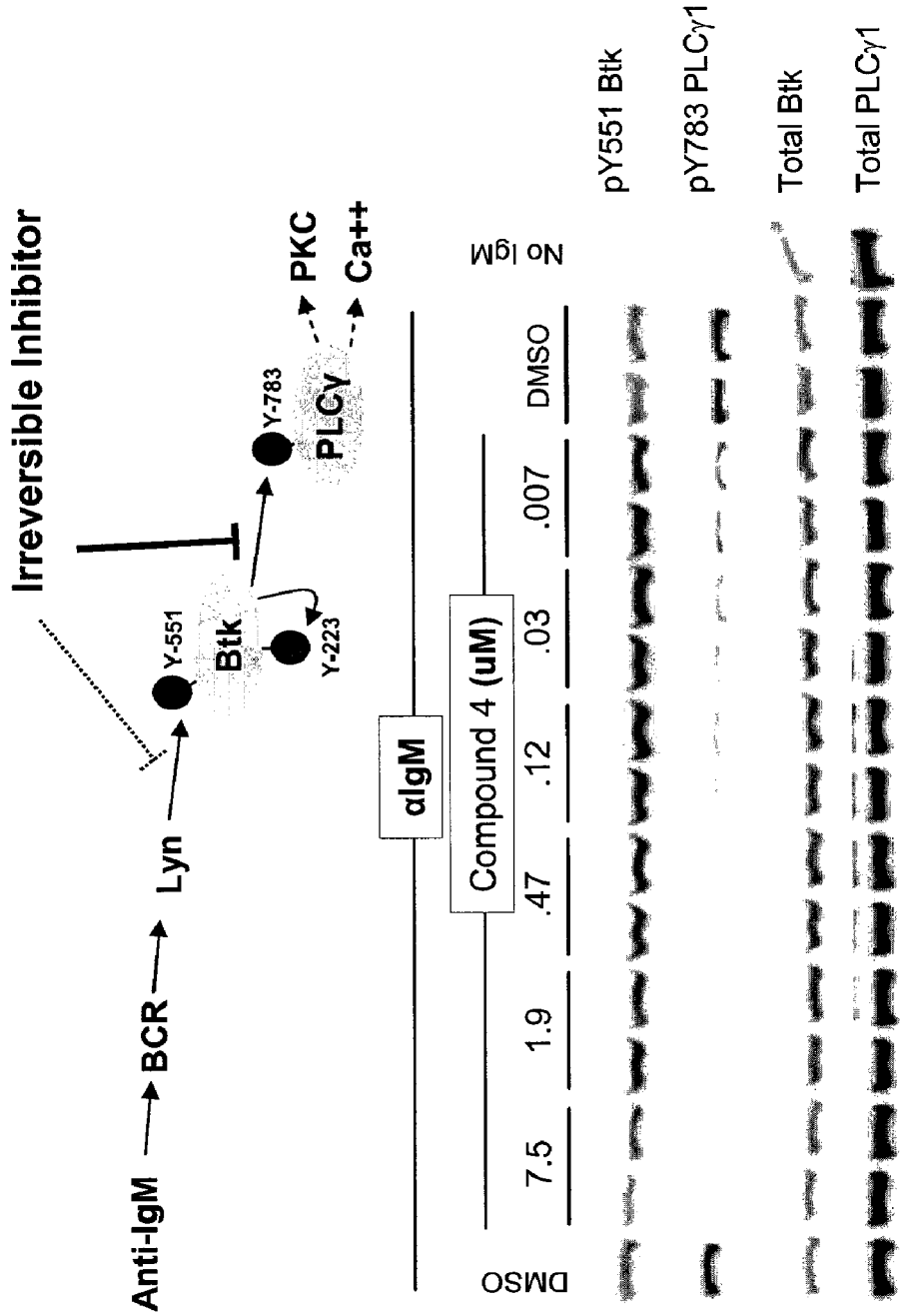
FIG. 2 presents illustrative cell data regarding inhibition of B cell receptor induced Phospholipase-Cγ phosphorylation by compound 4. In this example, there were 2E6 Ramos cells/well in serum free media; the cells were pretreated with compound for 1.5 hr. The B cell receptor was stimulated with anti-IgM for 3 min; the 10× lysis buffer containing DNAse was added directly to cells. The sample buffer was added and loaded directly on gel. The samples were analyzed with western blot—phosphorylated Btk and PLCγ1 and total Btk and PLCγ1. The blot was imaged with ChemiDoc CCD and quantitated with ImageQuant. The phosphorylated band was normalized to total band and the IC50 was calculated.
Figure 3:
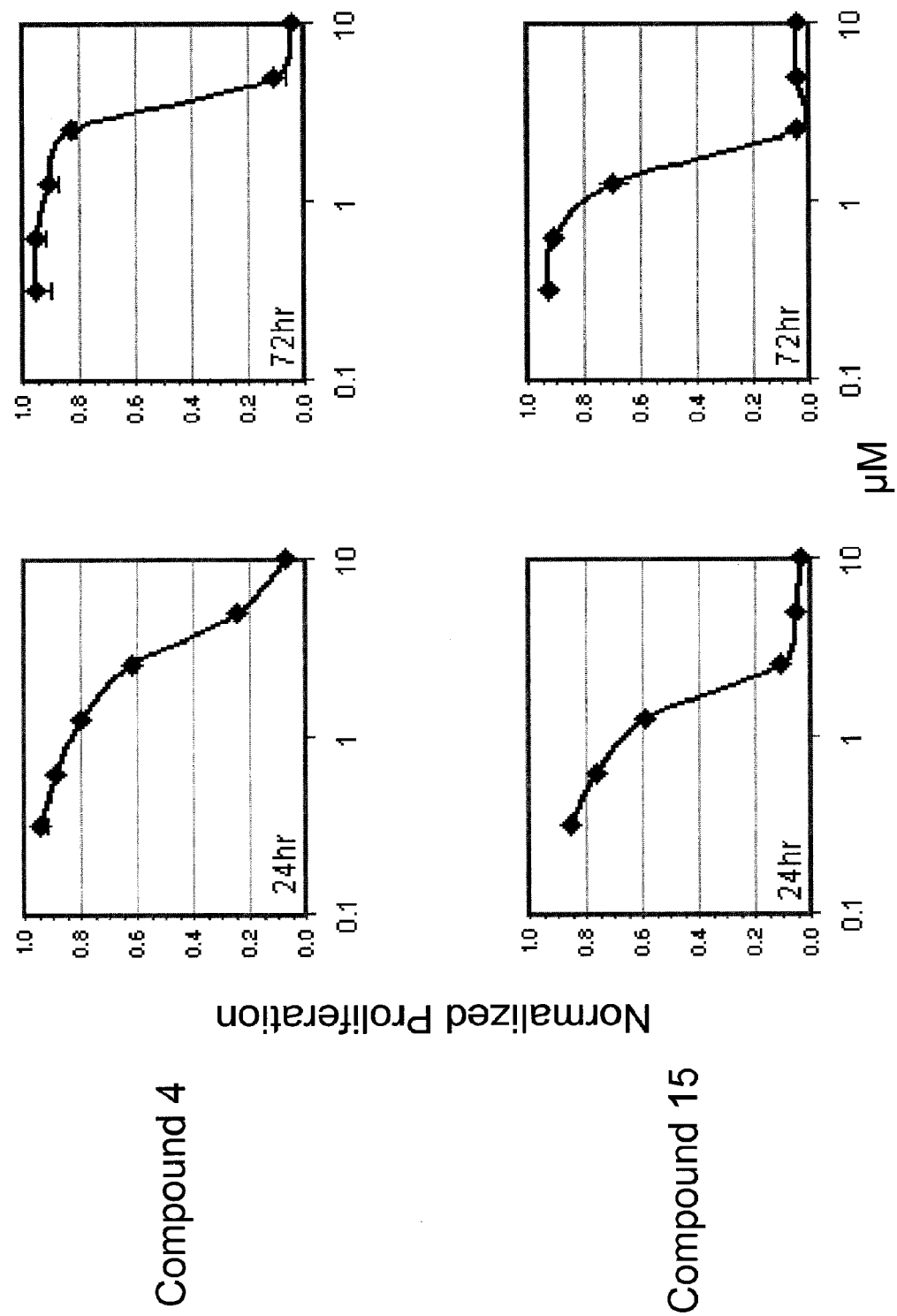
FIG. 3 presents illustrative cell data showing that compound 4 and compound 15 inhibit growth of DHL-6 cells. In this example, there were 3E4 DHL-6 cells/well in complete media. The cells were treated for the indicated time with compound @ 0.1% DMSO final concentration. The cell number was measured using Alamar Blue assay according to standard protocol.
Figure 4:
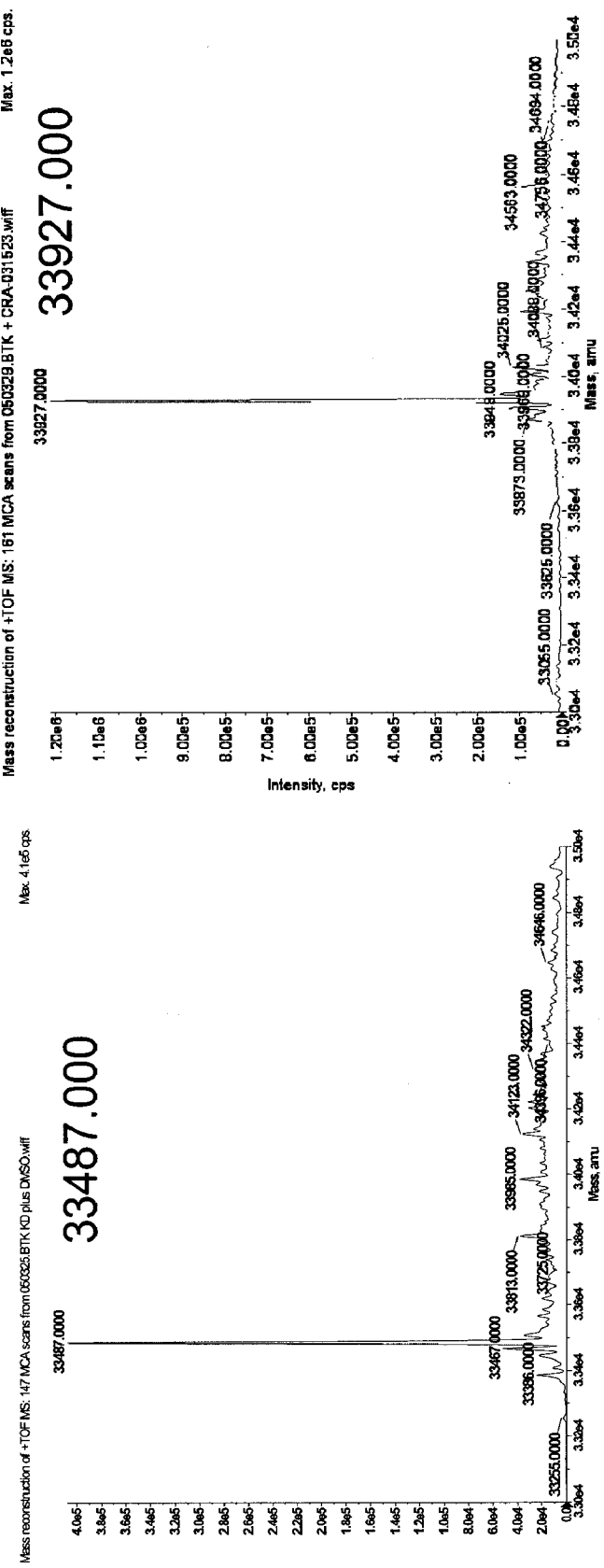
FIG. 4 presents illustrative mass spectra showing that compound 4 covalently modifies Btk. In this example, Incubate 30 uM compound 4 with 6-7 uM recombinant BTK (Y–>D mutant, kinase domain only) overnight at RT. Desalt protein-inhibitor complex by reversed-phase HPLC and analyze directly in mass spec to determine molecular weight. >99% of recombinant Btk protein is covalently modified by compound 4.
Figure 5:
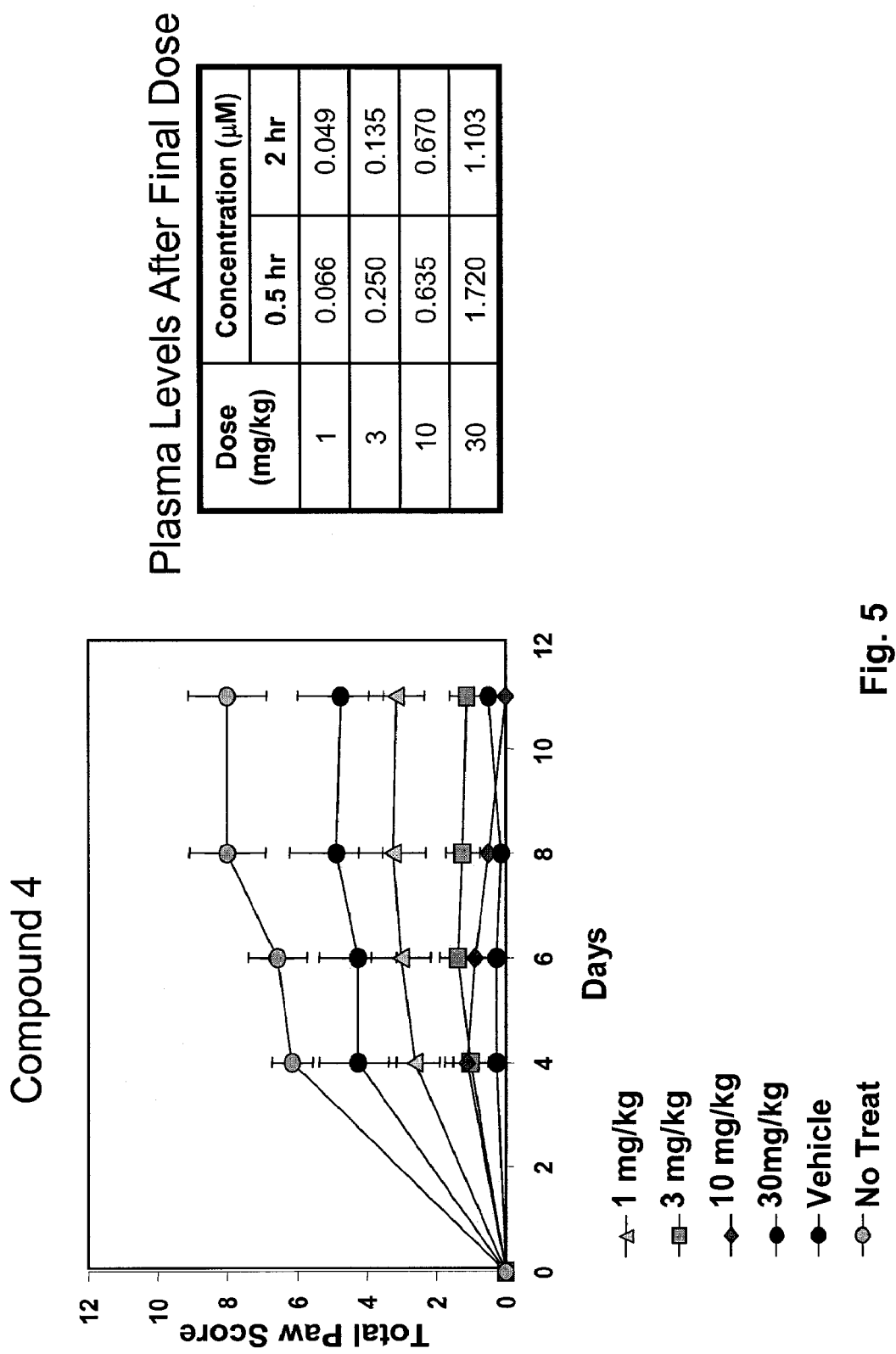
FIG. 5 presents illustrative inhibition of arthritis development in a mouse model by compound 4.
Figure 6:
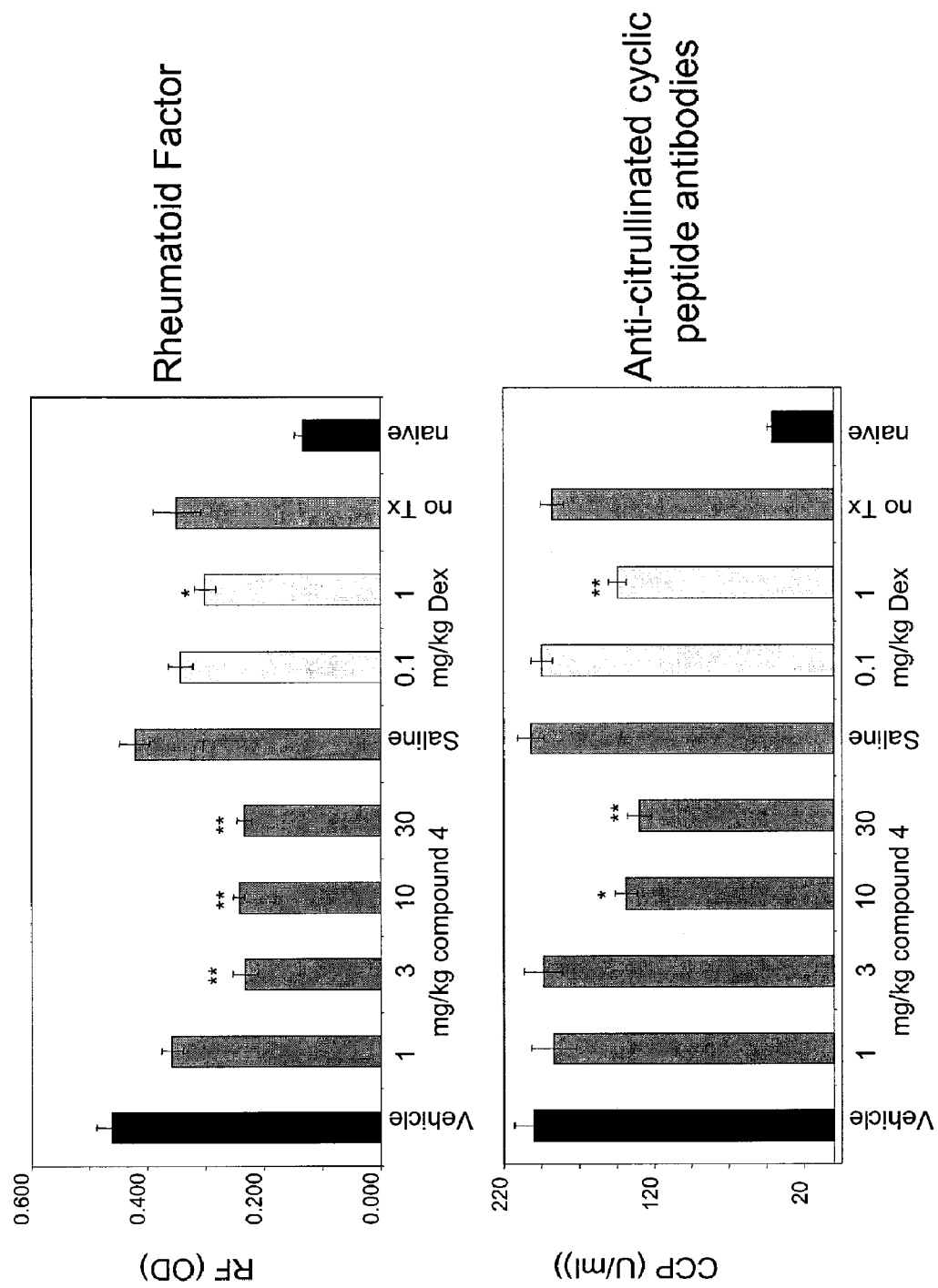
FIG. 6 presents illustrative data demonstrating that the efficacy of compound 4 is associated with reduction of Rheumatoid Factor and Anti-citrullinated cyclic peptide antibodies in the CAIA model. In these examples, *p<0.01; **p<0.001 vs vehicle or saline treatment.
Figure 7:
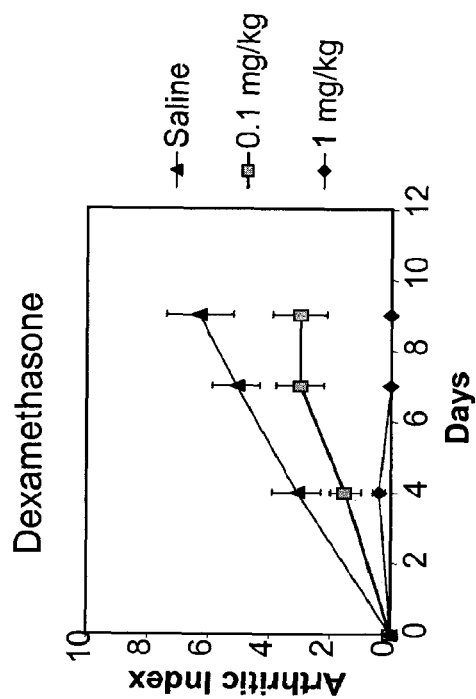
FIG. 7 presents illustrative data regarding the inhibition of arthritis development in a mouse model by compound 13. This enantiomer of compound 4 completed inhibited the development of arthritis in the CAIA model at dose levels of 10 and 30 mg/kg. For comparison, data regarding inhibition of arthritis development in the same mouse model is presented for dexamethasone.
Figure 7:
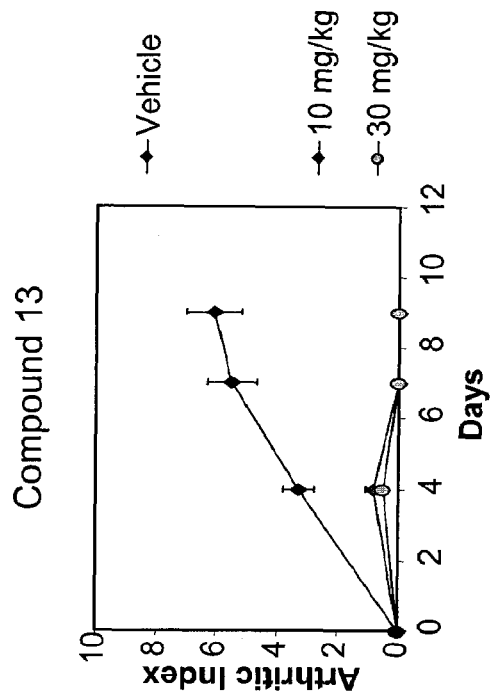

The methods described herein include administering to a subject in need a composition containing a therapeutically effective amount of one or more irreversible Btk inhibitor compounds described herein. Without being bound by theory, the diverse roles played by Btk signaling in various hematopoietic cell functions, e.g., B-cell receptor activation, show that small molecule Btk inhibitors are useful for reducing the risk of or treating a variety of diseases affected by or affecting many cell types of the hematopoetic lineage including, e.g., autoimmune diseases, heteroimmune conditions or diseases, inflammatory diseases, cancer (e.g., B-cell proliferative disorders), and thromboembolic disorders. Further, the irreversible Btk inhibitor compounds described herein can be used to inhibit a small subset of other tyrosine kinases that share homology with Btk by having a cysteine residue (including a Cys 481 residue) that can form a covalent bond with the irreversible inhibitor. See, e.g., protein kinases in FIG. 1. Thus, a subset of tyrosine kinases other than Btk are also expected to be useful as therapeutic targets in a number of health conditions.

In some embodiments, the methods described herein can be used to treat an autoimmune disease, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

In some embodiments, the methods described herein can be used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In further embodiments, the methods described herein can be used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Symptoms, diagnostic tests, and prognostic tests for each of the above-mentioned conditions include, e.g., *Harrison's Principles of Internal Medicine©*," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of irreversible Btk inhibitor compounds for treating any of the foregoing diseases.

For example, dosing of irreversible Btk inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837.

In another example, dosing of irreversible Btk inhibitors for the treatment of B-cell proliferative disorders can be examined in, e.g., a human-to-mouse xenograft model in which human B-cell lymphoma cells (e.g. Ramos cells) are implanted into immunodeficient mice (e.g., "nude" mice) as described in, e.g., Pagel et al. (2005), Clin Cancer Res 11(13): 4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo Btk activity achieved by administering a given dose of an irreversible Btk inhibitor. Cellular assays can be used to determine in vivo activity of Btk in the presence or absence of an irreversible Btk inhibitor. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor compound that is administered to a subject can be increased or decreased as needed so as to maintain a level of Btk inhibition optimal for treating the subject's disease state.

Compounds

In the following description of irreversible Btk compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. In addition, nucleic acid and amino acid sequences for Btk (e.g., human Btk) are disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients The Btk inhibitor compounds described herein are selective for Btk and kinases having a cysteine residue in an amino acid sequence position of the tyrosine kinase that is homologous to the amino acid sequence position of cysteine 481 in Btk. See, e.g., kinases in FIG. 1. Inhibitor compounds described herein include a Michael acceptor moiety.

Generally, an irreversible inhibitor compound of Btk used in the methods described herein is identified or characterized in an in vitro assay, e.g., an acellular biochemical assay or a cellular functional assay. Such assays are useful to determine an in vitro $IC_{50}$ for an irreversible Btk inhibitor compound.

For example, an acellular kinase assay can be used to determine Btk activity after incubation of the kinase in the absence or presence of a range of concentrations of a candidate irreversible Btk inhibitor compound. If the candidate compound is in fact an irreversible Btk inhibitor, Btk kinase activity will not be recovered by repeat washing with inhibitor-free medium. See, e.g., J. B. Smaill, et al. (1999), *J. Med. Chem.* 42(10):1803-1815. Further, covalent complex formation between Btk and a candidate irreversible Btk inhibitor is a useful indicator of irreversible inhibition of Btk that can be readily determined by a number of methods (e.g., mass spectrometry). For example, some irreversible Btk-inhibitor compounds can form a covalent bond with Cys 481 of Btk (e.g., via a Michael reaction).

Cellular functional assays for Btk inhibition include measuring one or more cellular endpoints in response to stimulating a Btk-mediated pathway in a cell line (e.g., BCR activation in Ramos cells) in the absence or presence of a range of concentrations of a candidate irreversible Btk inhibitor compound. Useful endpoints for determining a response to BCR activation include, e.g., autophosphorylation of Btk, phosphorylation of a Btk target protein (e.g., PLC-γ), and cytoplasmic calcium flux.

High throughput assays for many acellular biochemical assays (e.g., kinase assays) and cellular functional assays (e.g., calcium flux) are documented methodologies. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of irreversible Btk compounds without undue effort.

Irreversible Btk inhibitor compounds can used for the manufacture of a medicament for treating any of the foregoing conditions (e.g., autoimmune diseases, inflammatory diseases, allergy disorders, B-cell proliferative disorders, or thromboembolic disorders).

In some embodiments, the irreversible Btk inhibitor compound used for the methods described herein inhibits Btk or a Btk homolog kinase activity with an in vitro $IC_{50}$ of less than 10 μM. (e.g., less than 1 μM, less than 0.5 μM, less than 0.4 μM, less than 0.3 μM, less than 0.1, less than 0.08 μM, less than 0.06 μM, less than 0.05 μM, less than 0.04 μM, less than 0.03 μM, less than less than 0.02 μM, less than 0.01, less than 0.008 μM, less than 0.006 μM, less than 0.005 μM, less than 0.004 μM, less than 0.003 μM, less than less than 0.002 μM, less than 0.001, less than 0.00099 μM, less than 0.00098 μM, less than 0.00097 μM, less than 0.00096 μM, less than 0.00095 μM, less than 0.00094 μM, less than 0.00093 μM, less than 0.00092, or less than 0.00090 μM).

In one embodiment, the irreversible Btk inhibitor compound selectively and irreversibly inhibits an activated form of its target tyrosine kinase (e.g., a phosphorylated form of the tyrosine kinase). For example, activated Btk is transphosphorylated at tyrosine 551. Thus, in these embodiments the irreversible Btk inhibitor inhibits the target kinase in cells only once the target kinase is activated by the signaling events.

Described herein are compounds of any of Formula (A1-A6), Formula (B1-B6), Formula (C1-C6), or Formula (D1-D6). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom is optionally converted to an N-oxide. In certain embodiments, isomers and chemically protected forms of compounds having a structure represented by any of Formula (A1-A6), Formula (B1-B6), Formula (C1-C6), or Formula (D1-D6), are also provided.

In one aspect are compounds of Formula (A1-A6), pharmaceutically acceptable salts, pharmaceutically active metabolites, pharmaceutically acceptable prod rugs, and pharmaceutically acceptable solvates thereof. Formula (A1-A6) are as follows:

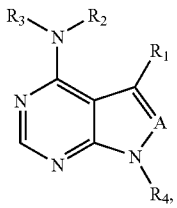

Formula (A1)

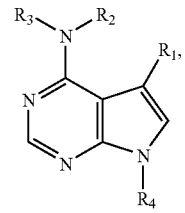

Formula (A2)

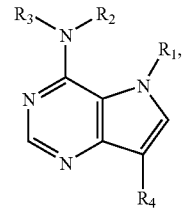

Formula (A3)

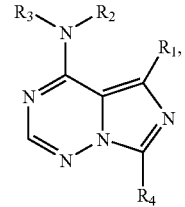

Formula (A4)

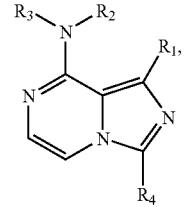

Formula (A5)

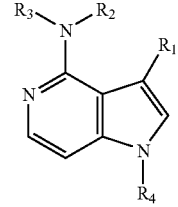

Formula (A6)

wherein
  A is independently selected from N or $CR_5$;
  $R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);
  $R_2$ and $R_3$ are independently selected from H, lower alkyl and substituted lower alkyl;
  $R_4$ is $L_3$-X-$L_4$-G, wherein,
    $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, O, —C(=O), S, —S(=O), —S(=O)₂, —NH, —NR₉, —NHC(O), —C(O)NH, —NR₉C(O), —C(O)NR₉, —S(=O)₂NH, —NHS(=O)₂, —S(=O)₂NR₉—, —NR₉S (=O)₂, —OC(O)NH—, —NHC(O)O—, —OC(O)NR₉—, —NR₉C(O)O—, —CH=NO—, —ON=CH—, —NR₁₀C(O)NR₁₀—, heteroaryl, aryl, —NR₁₀C(=NR₁₁)NR₁₀—, —NR₁₀C(=NR₁₁)—, —C(=NR₁₁)NR₁₀—, —OC(=NR₁₁)—, or —C(=NR₁₁)O—;

L₄ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or L₃, X and L₄ taken together form a nitrogen containing heterocyclic ring;

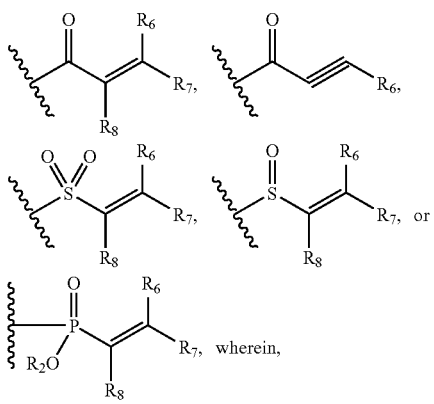

wherein,

G is

R₆, R₇ and R₈ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

R₅ is H, halogen, -L₆-(substituted or unsubstituted C₁-C₃ alkyl), -L₆-(substituted or unsubstituted C₂-C₄ alkenyl), -L₆-(substituted or unsubstituted heteroaryl), or L₆-(substituted or unsubstituted aryl), wherein L₆ is a bond, O, S, —S(=O), S(=O)₂, NH, C(O), —NHC(O)O, —OC(O)NH, —NHC(O), or —C(O)NH;

each R₉ is independently selected from among H, substituted or unsubstituted lower alkyl, and substituted or unsubstituted lower cycloalkyl;

each R₁₀ is independently H, substituted or unsubstituted lower alkyl, or substituted or unsubstituted lower cycloalkyl; or two R₁₀ groups can together form a 5-, 6-, 7-, or 8-membered heterocyclic ring; or R₉ and R₁₀ can together form a 5-, 6-, 7-, or 8-membered heterocyclic ring; or each R₁₁ is independently selected from H, S(=O)₂R₈, S(=O)₂NH₂, —C(O)R₈, —CN, —NO₂, heteroaryl, or heteroalkyl; and pharmaceutically active metabolites, pharmaceutically acceptable solvates, pharmaceutically acceptable salts, or pharmaceutically acceptable prodrugs thereof.

In a further or alternative embodiment, the compound of Formula (A1-A6) has the following structure of Formula (B1-B6):

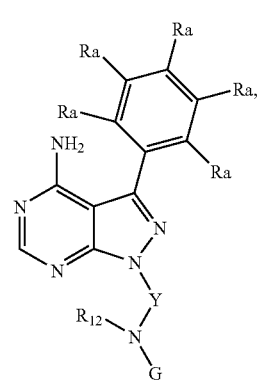

Formula (B1)

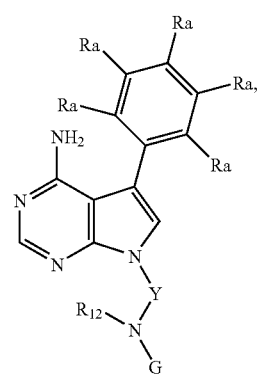

Formula (B2)

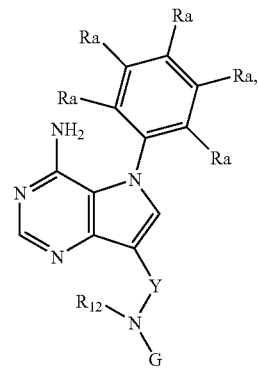

Formula (B3)

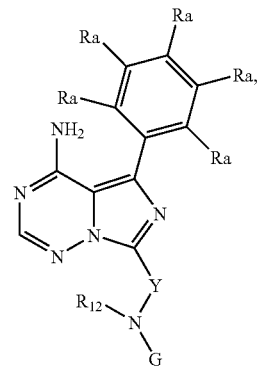

Formula (B4)

-continued

Formula (B5)

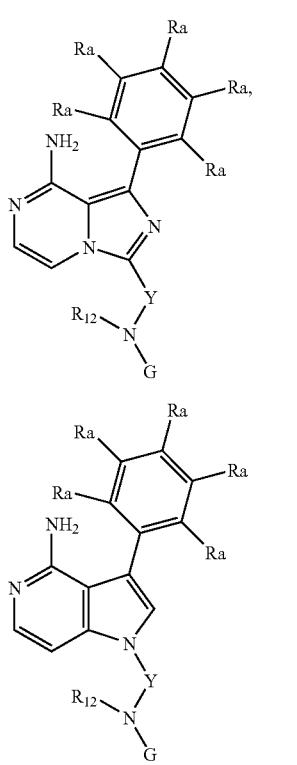

Formula (B6)

wherein:
Y is alkyl or substituted alkyl, or a 4-, 5-, or 6-membered cycloalkyl ring;
each $R_a$ is independently H, halogen, —$CF_3$, —CN, —$NO_2$, OH, $NH_2$, -$L_a$-(substituted or unsubstituted alkyl), -$L_a$-(substituted or unsubstituted alkenyl), -$L_a$-(substituted or unsubstituted heteroaryl), or -$L_a$-(substituted or unsubstituted aryl), wherein $L_a$ is a bond, O, S, —S(=O), —S(=O)$_2$, NH, C(O), $CH_2$, —NHC(O)O, —NHC(O), or —C(O)NH;
G is

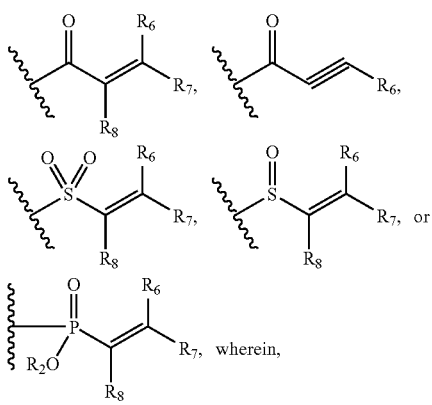

$R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_{12}$ is H or lower alkyl; or
Y and $R_{12}$ taken together form a 4-, 5-, or 6-membered heterocyclic ring; and
pharmaceutically acceptable active metabolites, pharmaceutically acceptable solvates, pharmaceutically acceptable salts, or pharmaceutically acceptable prodrugs thereof.

In further or alternative embodiments, G is selected from among

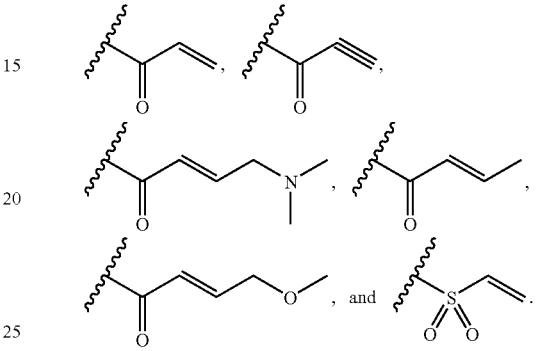

In further or alternative embodiments,

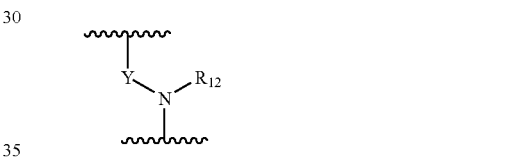

is selected from among

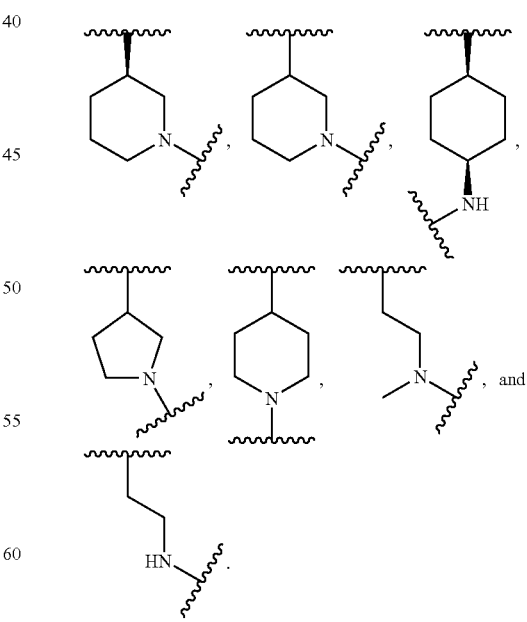

In further or alternative embodiment, the compound of Formula (B1-B6) has the following structure of Formula (C1-C6):

Formula (C1), Formula (C2), Formula (C3), Formula (C4), Formula (C5), Formula (C6)

Y is alkyl or substituted alkyl, or a 4-, 5-, or 6-membered cycloalkyl ring;
$R_{12}$ is H or lower alkyl; or
Y and $R_{12}$ taken together form a 4-, 5-, or 6-membered heterocyclic ring;
G is $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl; and pharmaceutically acceptable active metabolites, pharmaceutically acceptable solvates, pharmaceutically acceptable salts, or pharmaceutically acceptable prodrugs thereof.

In a further or alternative embodiment, the "G" group of any of Formula (A1-A6), Formula (B1-B6), or Formula (C1-C6) is any group that is used to tailor the physical and biological properties of the molecule. Such tailoring/modifications are achieved using groups which modulate Michael acceptor chemical reactivity, acidity, basicity, lipophilicity, solubility and other physical properties of the molecule. The physical and biological properties modulated by such modifications to G include, by way of example only, enhancing chemical reactivity of Michael acceptor group, solubility, in vivo absorption, and in vivo metabolism. In addition, in vivo metabolism may include, by way of example only, controlling in vivo PK properties, off-target activities, potential toxicities associated with cypP450 interactions, drug-drug interactions, and the like. Further, modifications to G allow for the tailoring of the in vivo efficacy of the compound through the modulation of, by way of example, specific and non-specific protein binding to plasma proteins and lipids and tissue distribution in vivo.

In a further embodiment are compounds having the structures of Formula (D1-D6):

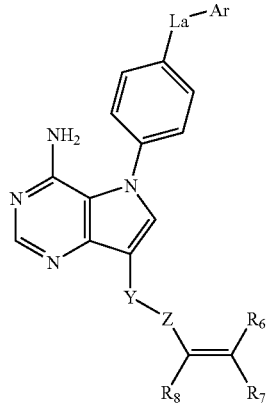

Formula (D1)

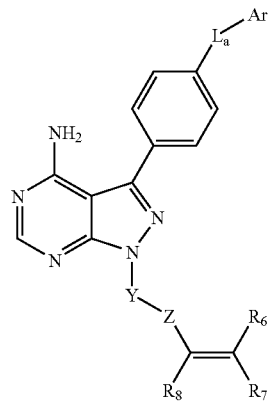

Formula (D2)

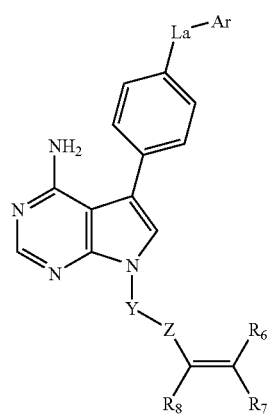

-continued

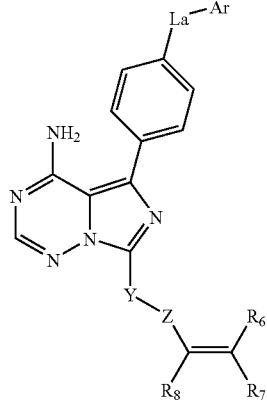

Formula (D3)

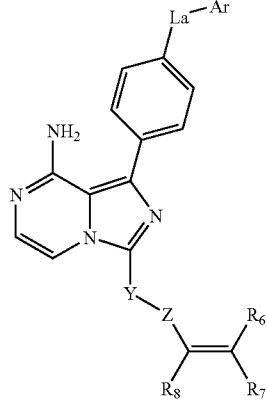

Formula (D4)

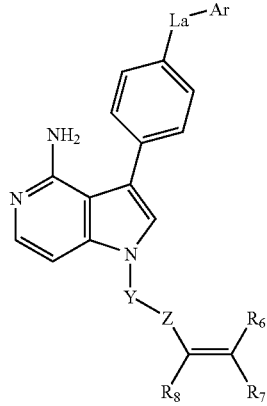

Formula (D5)

Formula (D6)

wherein
  $L_a$ is $CH_2$, O, NH or S;
  Ar is an optionally substituted aromatic carbocycle or an aromatic heterocycle;
  Y is an optionally substituted alkyl, heteroalkyl, carbocycle, heterocycle, or combination thereof;
  Z is C(O), OC(O), NHC(O), C(S), $S(O)_x$, $OS(O)_x$, $NHS(O)_x$, where x is 1 or 2; and
  $R_6$, $R_7$, and $R_8$ are independently selected from H, alkyl heteroalkyl, carbocycle, heterocycle, or combinations thereof.

In a further or alternative embodiment, $L_a$ is O.
In a further or alternative embodiment, Ar is phenyl.
In a further or alternative embodiment, Z is C(O).
In a further or alternative embodiment, each of $R_1$, $R_2$, and $R_3$ is H.

In another embodiment, provided herein are compounds of Formula (D1-D6). Formula (D1-D6) are as follows:

Formula (D1)

Formula (D2)

Formula (D3)

Formula (D4)

Formula (D5)

Formula (D6)

wherein:
  $L_a$ is $CH_2$, O, NH or S;
  Ar is a substituted or unsubstituted aryl, or a substituted or unsubstituted heteroaryl;
  Y is an optionally substituted group selected from among alkyl, heteroalkyl, cycloalkyl, heterocycloalkyl, aryl, and heteroaryl;
  Z is C(=O), OC(=O), NHC(=O), C(=S), $S(=O)_x$, $OS(=O)_x$, $NHS(=O)_x$, where x is 1 or 2;
  $R_7$ and $R_8$ are independently selected from among H, unsubstituted $C_1$-$C_4$alkyl, substituted $C_1$-$C_4$alkyl, unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or $R_7$ and $R_8$ taken together form a bond;

$R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl); and pharmaceutically active metabolites, or pharmaceutically acceptable solvates, pharmaceutically acceptable salts, or pharmaceutically acceptable prodrugs thereof.

For any and all of the embodiments, substituents can be selected from among from a subset of the listed alternatives. For example, in some embodiments, $L_a$ is $CH_2$, O, or NH. In other embodiments, $L_a$ is O or NH. In yet other embodiments, $L_a$ is O.

In some embodiments, Ar is a substituted or unsubstituted aryl. In yet other embodiments, Ar is a 6-membered aryl. In some other embodiments, Ar is phenyl.

In some embodiments, x is 2. In yet other embodiments, Z is C(=O), OC(=O), NHC(=O), S(=O)$_x$, OS(=O)$_x$, or NHS(=O)$_x$. In some other embodiments, Z is C(=O), NHC(=O), or S(=O)$_2$.

In some embodiments, $R_7$ and $R_8$ are independently selected from among H, unsubstituted $C_1$-$C_4$ alkyl, substituted $C_1$-$C_4$alkyl, unsubstituted $C_1$-$C_4$heteroalkyl, and substituted $C_1$-$C_4$heteroalkyl; or $R_7$ and $R_8$ taken together form a bond. In yet other embodiments, each of $R_7$ and $R_8$ is H; or $R_7$ and $R_8$ taken together form a bond.

In some embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-N($C_1$-$C_3$alkyl)$_2$, substituted or unsubstituted aryl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In some other embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-N($C_1$-$C_3$alkyl)$_2$, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In yet other embodiments, $R_6$ is H, substituted or unsubstituted $C_1$-$C_4$alkyl, —$CH_2$—O—($C_1$-$C_3$alkyl), —$CH_2$—N($C_1$-$C_3$alkyl)$_2$, $C_1$-$C_4$alkyl(phenyl), or $C_1$-$C_4$alkyl(5- or 6-membered heteroaryl). In some embodiments, $R_6$ is H, substituted or unsubstituted $C_1$-$C_4$alkyl, —$CH_2$—O—($C_1$-$C_3$alkyl), —$CH_2$—N($C_1$-$C_3$alkyl)$_2$, $C_1$-$C_4$alkyl(phenyl), or $C_1$-$C_4$alkyl(5- or 6-membered heteroaryl containing 1 or 2 N atoms), or $C_1$-$C_4$alkyl(5- or 6-membered heterocycloalkyl containing 1 or 2 N atoms).

In some embodiments, Y is an optionally substituted group selected from among alkyl, heteroalkyl, cycloalkyl, and heterocycloalkyl. In other embodiments, Y is an optionally substituted group selected from among $C_1$-$C_6$alkyl, $C_1$-$C_6$heteroalkyl, 4-, 5-, 6- or 7-membered cycloalkyl, and 4-, 5-, 6- or 7-membered heterocycloalkyl. In yet other embodiments, Y is an optionally substituted group selected from among $C_1$-$C_6$alkyl, $C_1$-$C_6$heteroalkyl, 5-, or 6-membered cycloalkyl, and 5-, or 6-membered heterocycloalkyl containing 1 or 2 N atoms. In some other embodiments, Y is a 5-, or 6-membered cycloalkyl, or a 5-, or 6-membered heterocycloalkyl containing 1 or 2 N atoms.

Any combination of the groups described above for the various variables is contemplated herein.

Further embodiments of compounds of Formula (A1-A6), Formula (B1-B6), Formula (C1-C6), Formula (D1-D6), include, but are not limited to, compounds selected from the group consisting of:

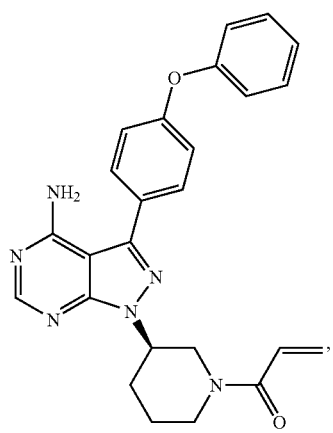

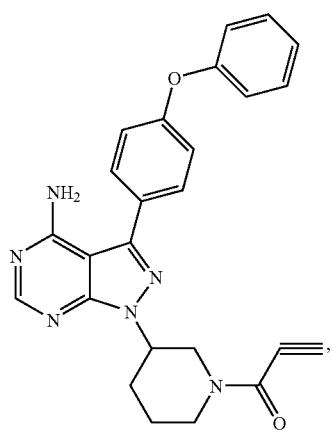

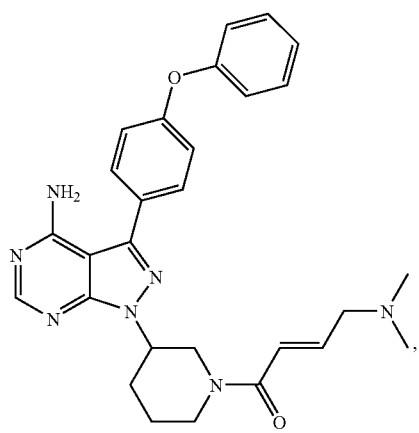

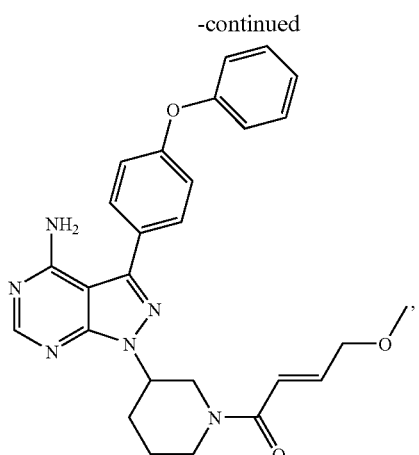
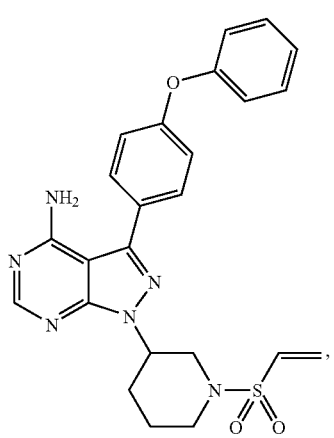
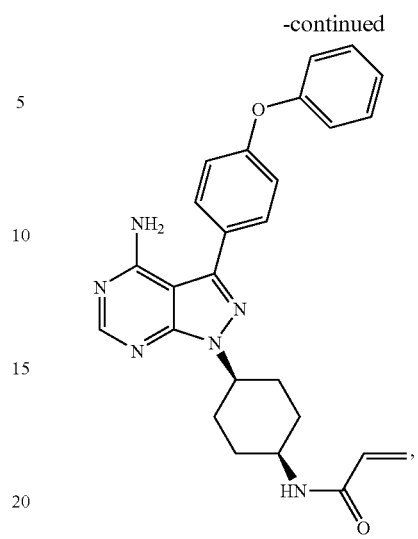
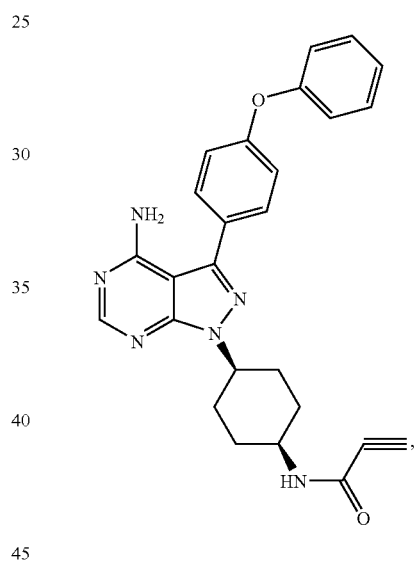
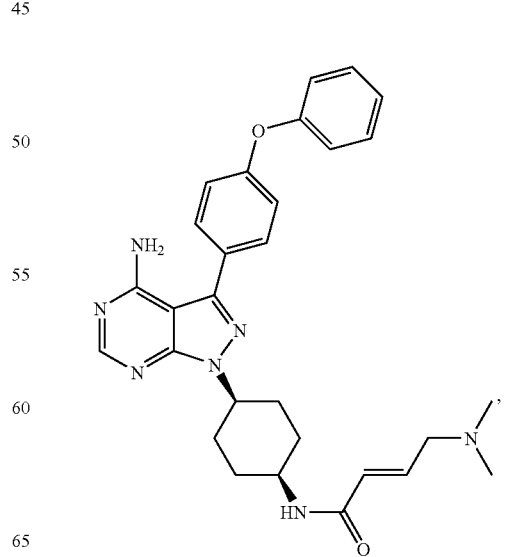

-continued
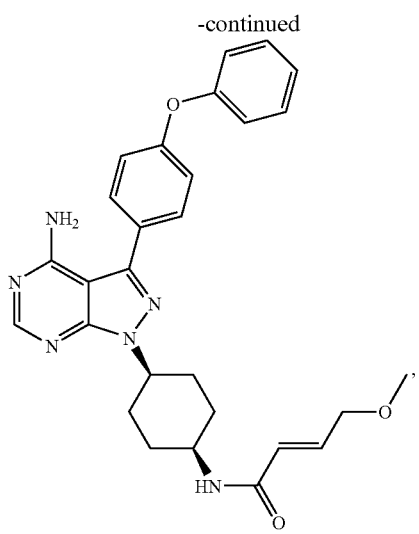
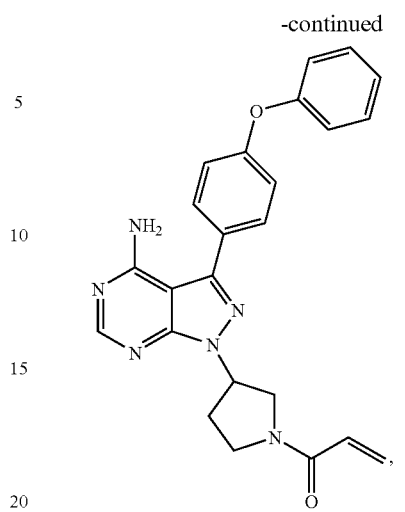
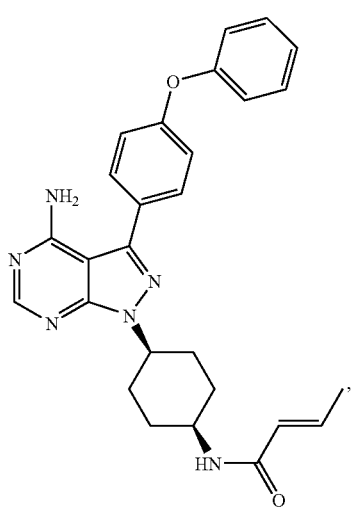
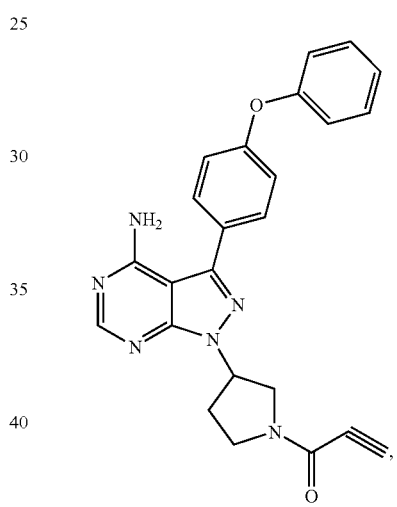
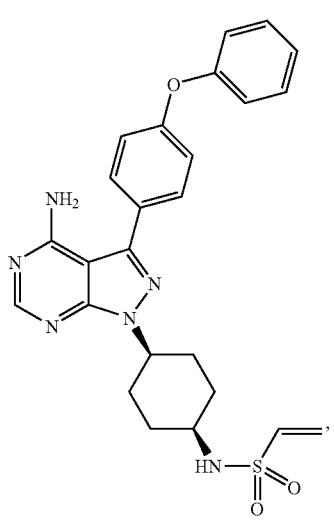
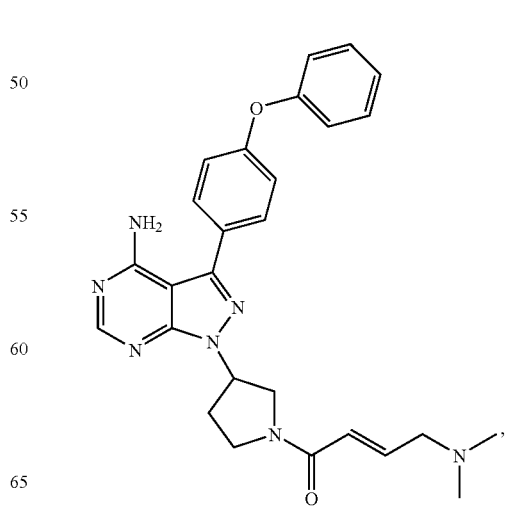

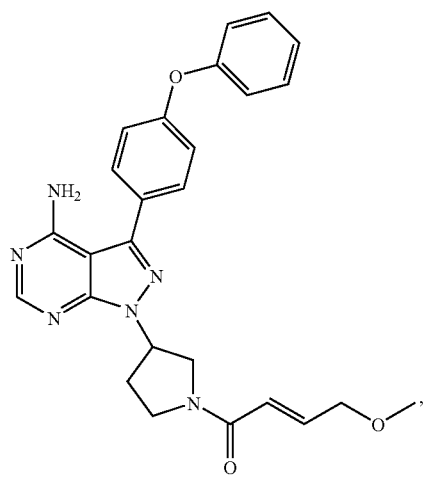
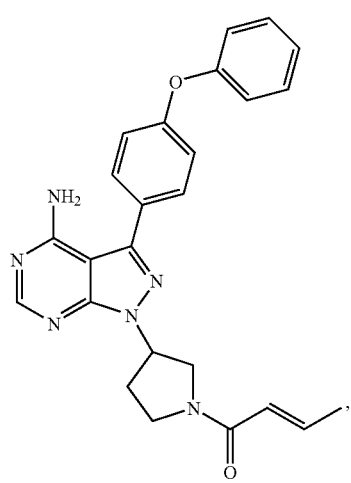
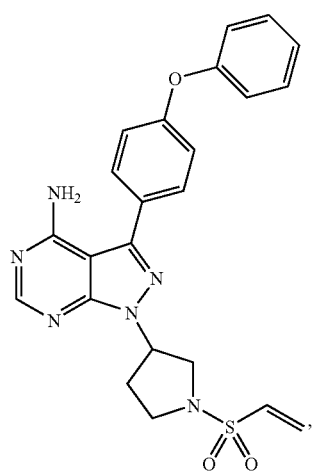
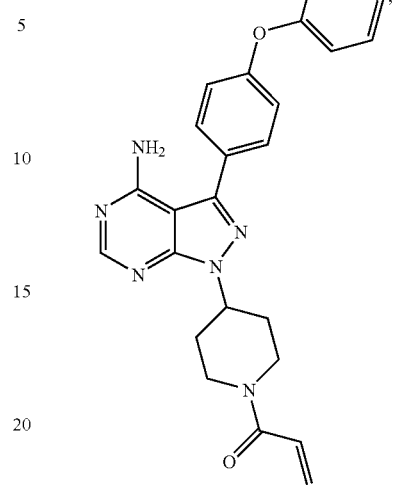
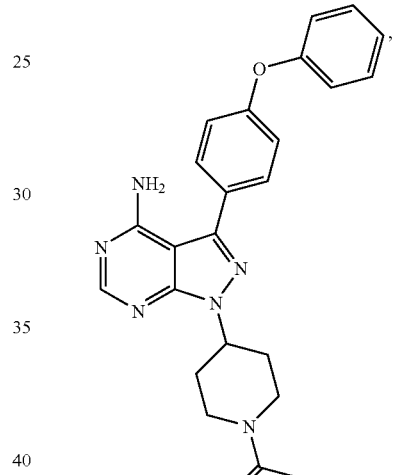

51
-continued
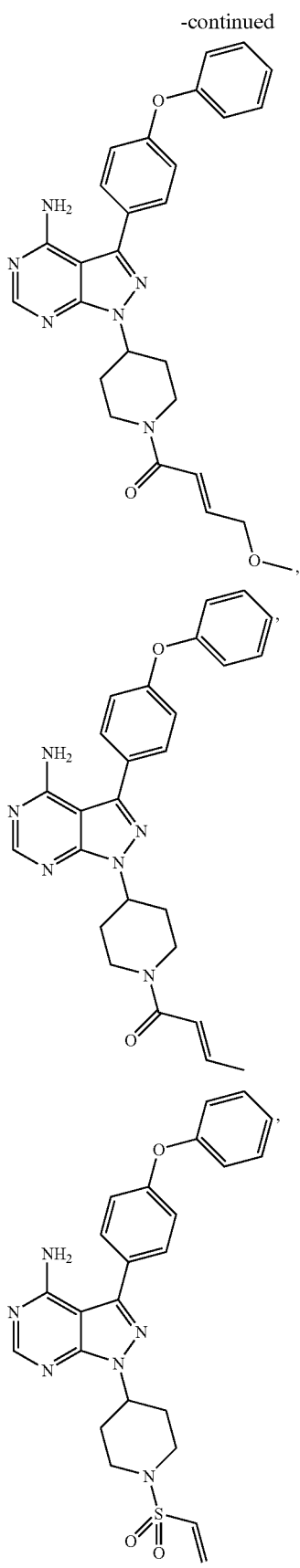
52
-continued
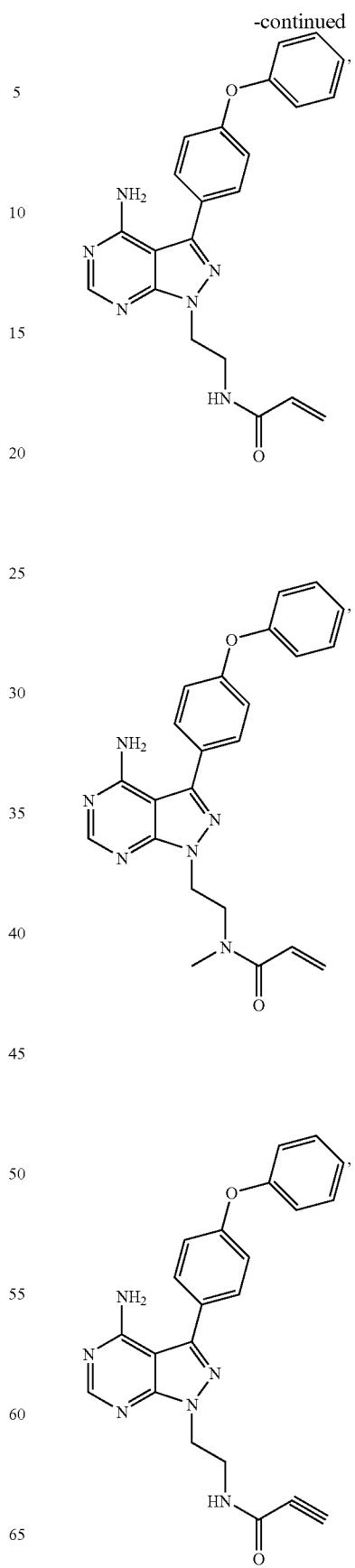

53
-continued
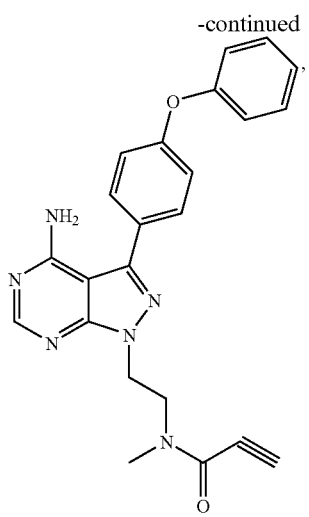
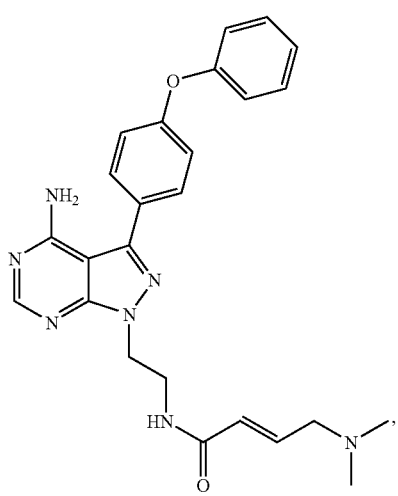
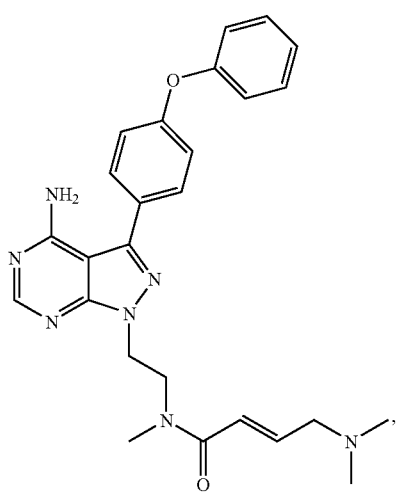
54
-continued
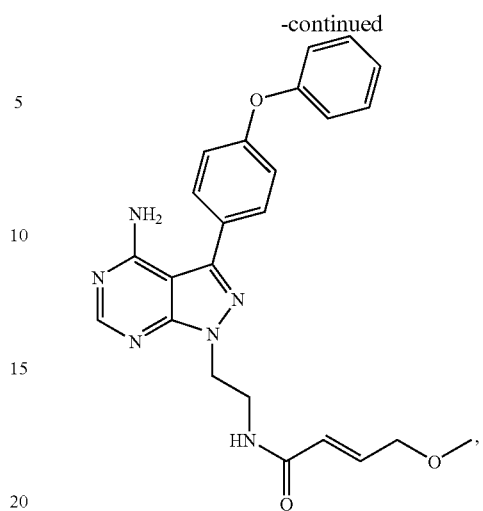
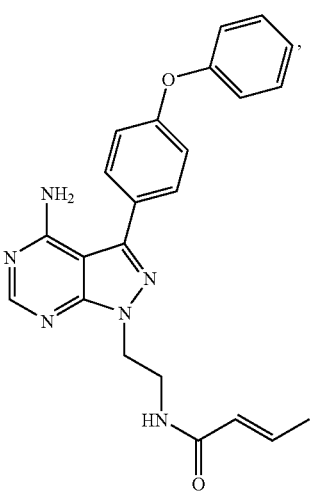

-continued
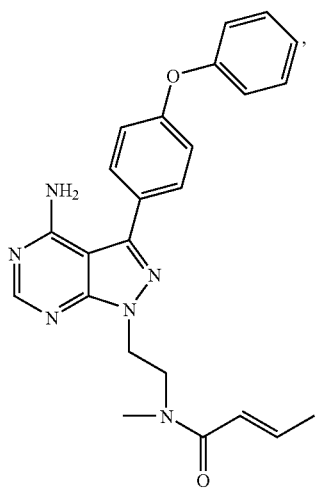
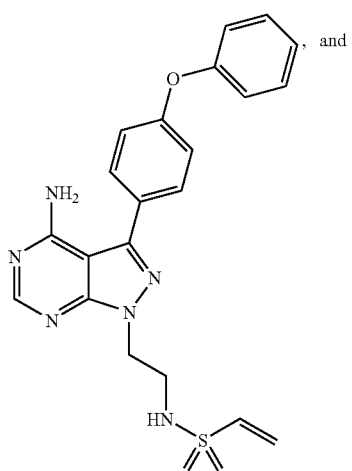, and
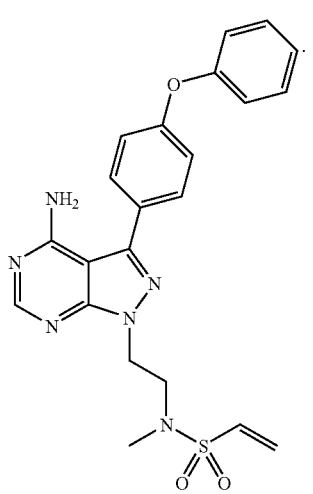
In still another embodiment, compounds provided herein are selected from among:
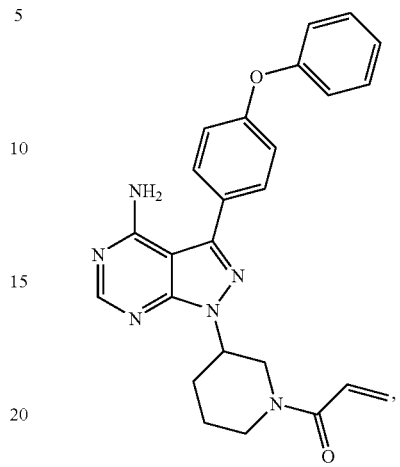
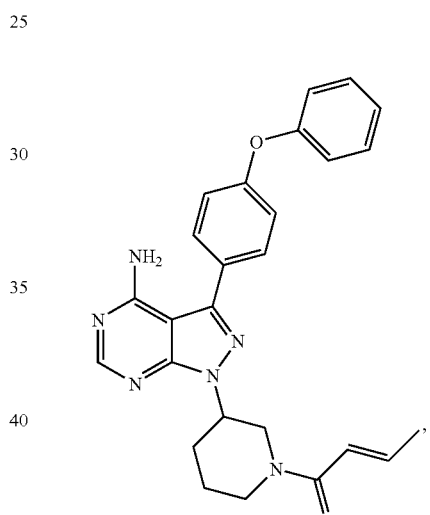
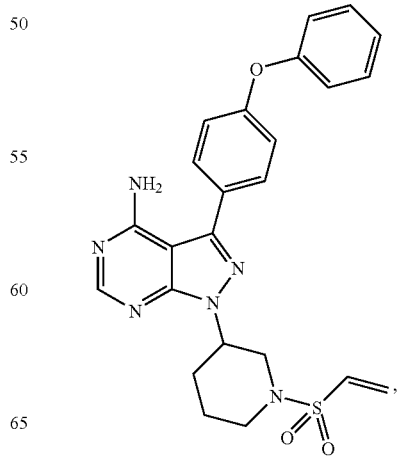

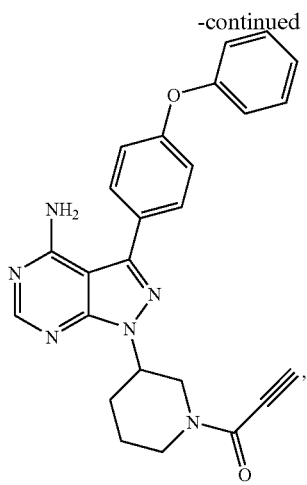
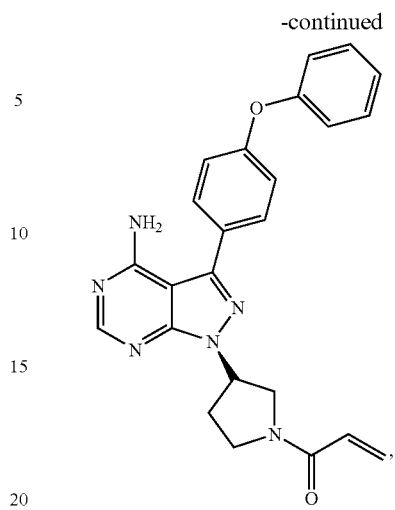
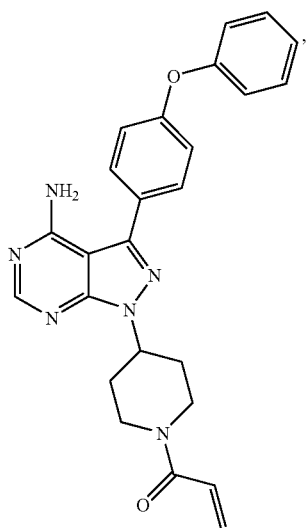
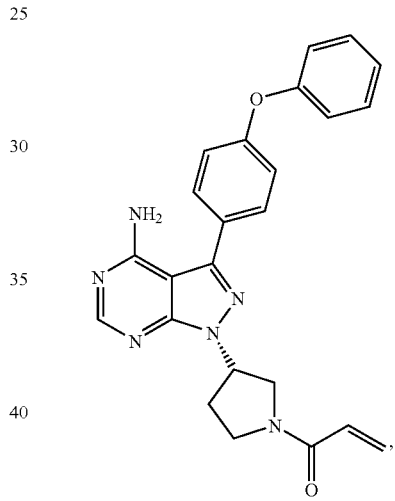
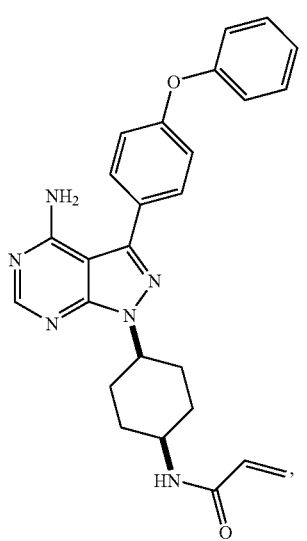
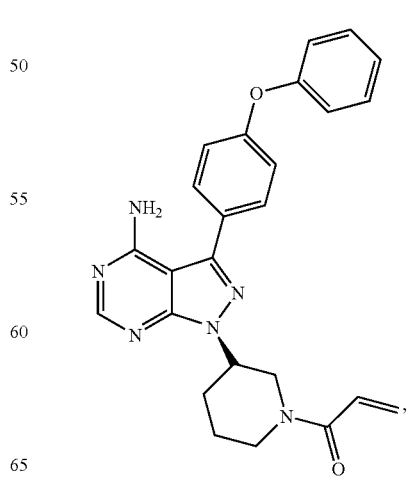

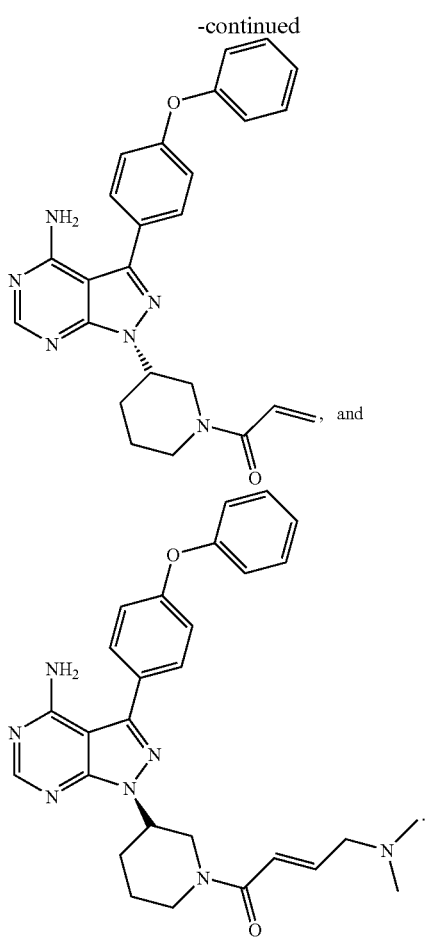

In one aspect, provided herein is a compound selected from among: 1-(3-(4-amino-3-(4-phenoxyphenyl)-1H-pyrazolo[3,4-d]pyrimidin-1-yl)piperidin-1-yl)prop-2-en-1-one (Compound 4); (E)-1-(3-(4-amino-3-(4-phenoxyphenyl)-1H-pyrazolo[3,4-d]pyrimidin-1-yl)piperidin-1-yl)but-2-en-1-one (Compound 5); 1-(3-(4-amino-3-(4-phenoxyphenyl)-1H-pyrazolo[3,4-d]pyrimidin-1-yl)piperidin-1-yl)sulfonylethene (Compound 6); 1-(3-(4-amino-3-(4-phenoxyphenyl)-1H-pyrazolo[3,4-d]pyrimidin-1-yl)piperidin-1-yl)prop-2-yn-1-one (Compound 8); 1-(4-(4-amino-3-(4-phenoxyphenyl)-1H-pyrazolo[3,4-d]pyrimidin-1-yl)piperidin-1-yl)prop-2-en-1-one (Compound 9); N-((1s,4s)-4-(4-amino-3-(4-phenoxyphenyl)-1H-pyrazolo[3,4-d]pyrimidin-1-yl)cyclohexyl)acrylamide (Compound 10); 1-((R)-3-(4-amino-3-(4-phenoxyphenyl)-1H-pyrazolo[3,4-d]pyrimidin-1-yl)pyrrolidin-1-yl)prop-2-en-1-one (Compound 11); 1-((S)-3-(4-amino-3-(4-phenoxyphenyl)-1H-pyrazolo[3,4-d]pyrimidin-1-yl)pyrrolidin-1-yl)prop-2-en-1-one (Compound 12); 1-((R)-3-(4-amino-3-(4-phenoxyphenyl)-1H-pyrazolo[3,4-d]pyrimidin-1-yl)piperidin-1-yl)prop-2-en-1-one (Compound 13); 1-((S)-3-(4-amino-3-(4-phenoxyphenyl)-1H-pyrazolo[3,4-d]pyrimidin-1-yl)piperidin-1-yl)prop-2-en-1-one (Compound 14); and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one (Compound 15).

The compounds of any of Formula (A1-A6), or Formula (B1-B6), or Formula (C1-C6), or Formula (D1-D6) can irreversibly inhibit Btk and may be used to treat patients suffering from Bruton's tyrosine kinase-dependent or Bruton's tyrosine kinase mediated conditions or diseases, including, but not limited to, cancer, autoimmune and other inflammatory diseases.

Preparation of Compounds

Compounds of any of Formula (A1-A6), (B1-B6), (C1-C6) or (D1-D6) are optionally synthesized using standard synthetic techniques or using such methods known in combination with methods described herein. In additions, solvents, temperatures and other reaction conditions are presented herein for illustration only, and not to limit the scope of the methods and compositions described herein. As a further guide the following synthetic methods may also be utilized.

The reactions are optionally employed in a linear sequence to provide the compounds described herein or used to synthesize fragments which are subsequently joined by the methods described herein and/or documented elsewhere.

Formation of Covalent Linkages by Reaction of an Electrophile with a Nucleophile The compounds described herein can be modified using various electrophiles or nucleophiles to form new functional groups or substituents. Table 1 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 1

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |

TABLE 1-continued

Examples of Covalent Linkages and Precursors Thereof

| Covalent Linkage Product | Electrophile | Nucleophile |
|---|---|---|
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |
| Alkyl thiol | α,β-unsaturated ester | thiols |
| Alkyl ethers | α,β-unsaturated ester | alcohols |
| Alkyl amines | α,β-unsaturated ester | amines |
| Alkyl thiol | Vinyl sulfone | thiols |
| Alkyl ethers | Vinyl sulfone | alcohols |
| Alkyl amines | Vinyl sulfone | amines |
| Vinyl sulfide | Propargyl amide | thiol |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

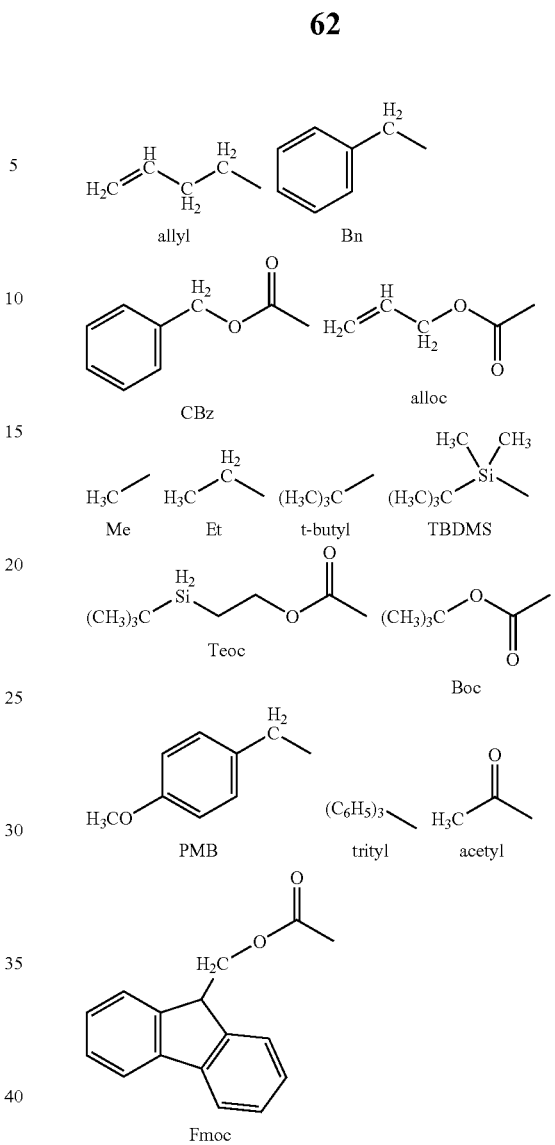

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Synthesis of Compounds

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

Described herein are compounds that inhibit the activity of tyrosine kinase(s), such as Btk, and processes for their preparation. Also described herein are pharmaceutically acceptable salts, pharmaceutically acceptable solvates, pharmaceutically active metabolites and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents are optionally synthesized using techniques and materials, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. As a guide the following synthetic methods may be utilized.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared using the synthetic methods described herein as a single isomer or a mixture of isomers.

A non-limiting example of a synthetic approach towards the preparation of compounds of any of Formula (A1-A6), (B1-B6), (C1-C6) or (D1-D6) is shown in Scheme I.

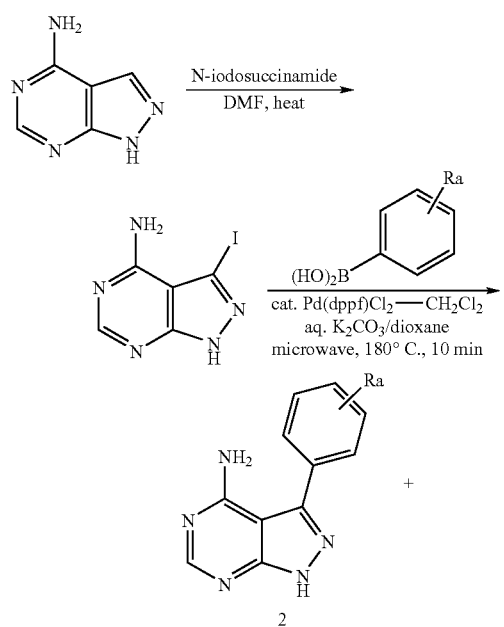

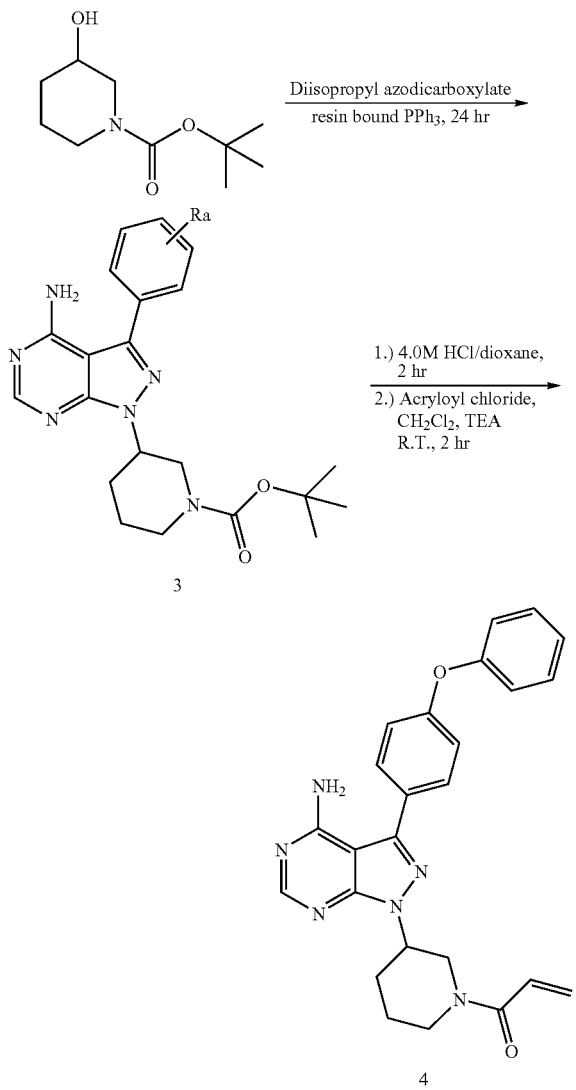

Halogenation of commercially available 1H-pyrazolo[3,4-d]pyrimidin-4-amine provides an entry into the synthesis of compounds of Formula (A1-A6), (B1-B6), (C1-C6) and/or (D1-D6). In one embodiment, 1H-pyrazolo[3,4-d]pyrimidin-4-amine is treated with N-iodosuccinamide to give 3-iodo-1H-pyrazolo[3,4-d]pyrimidin-4-amine. Metal catalyzed cross coupling reactions are then carried out on 3-iodo-1H-pyrazolo[3,4-d]pyrimidin-4-amine. In one embodiment, palladium mediated cross-coupling of a suitably substituted phenyl boronic acid under basic conditions constructs intermediate 2. Intermediate 2 is coupled with N-Boc-3-hydroxypiperidine (as non-limiting example) via Mitsunobu reaction to give the Boc (tert-butyloxycarbonyl) protected intermediate 3. After deprotection with acid, coupling with, but not limited to, an acid chloride, such as, but not limited to, acryloyl chloride, completes the synthesis to give compound 4.

A non-limiting example of a synthetic approach towards the preparation of compounds containing the imidazotriazine moiety,

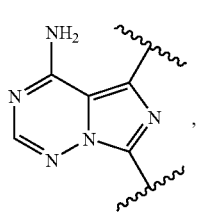
is shown in Scheme II.
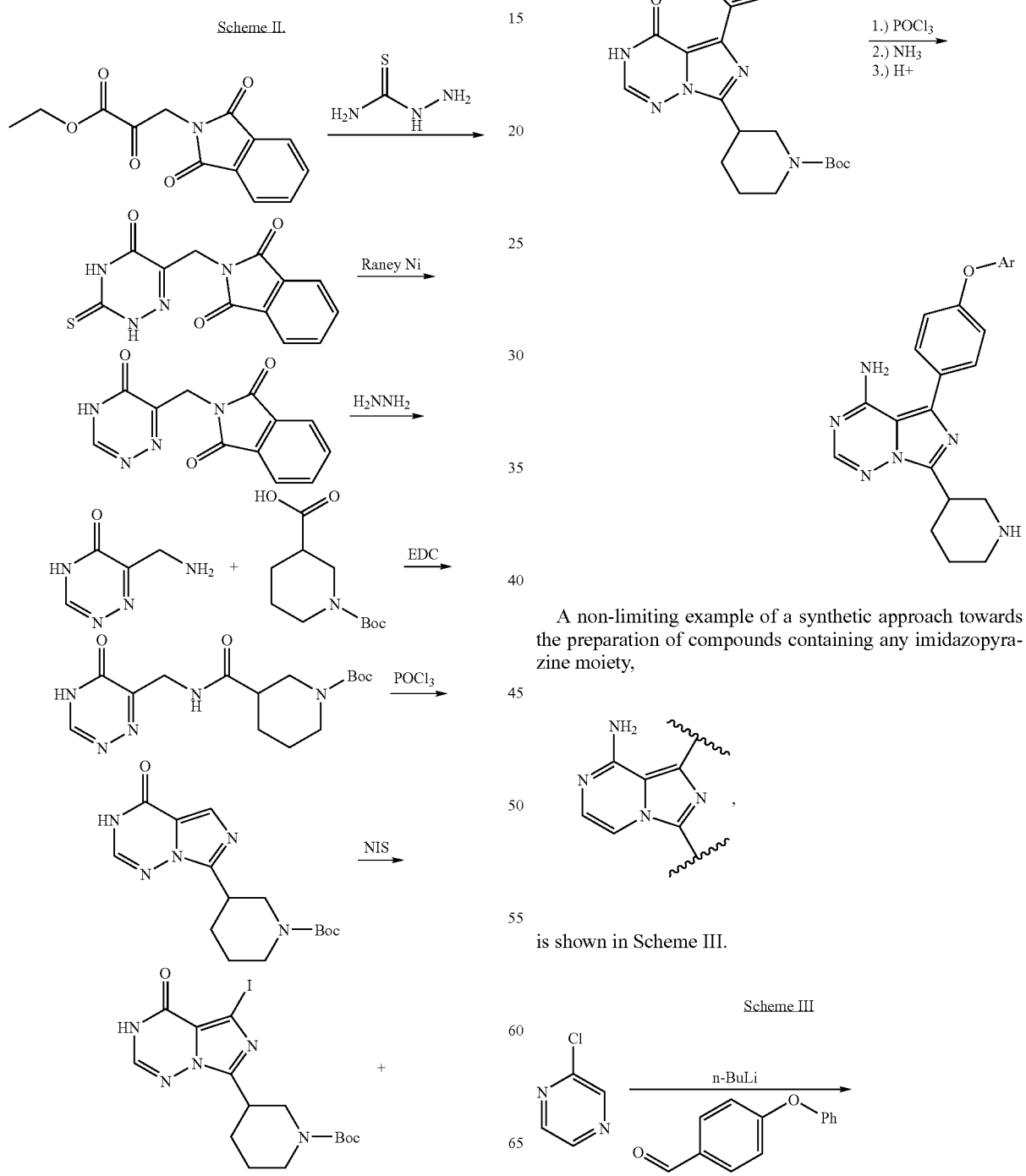
A non-limiting example of a synthetic approach towards the preparation of compounds containing any imidazopyrazine moiety,
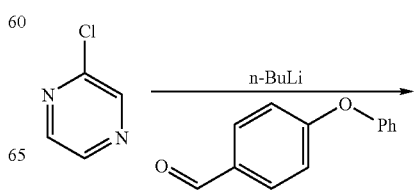
is shown in Scheme III.

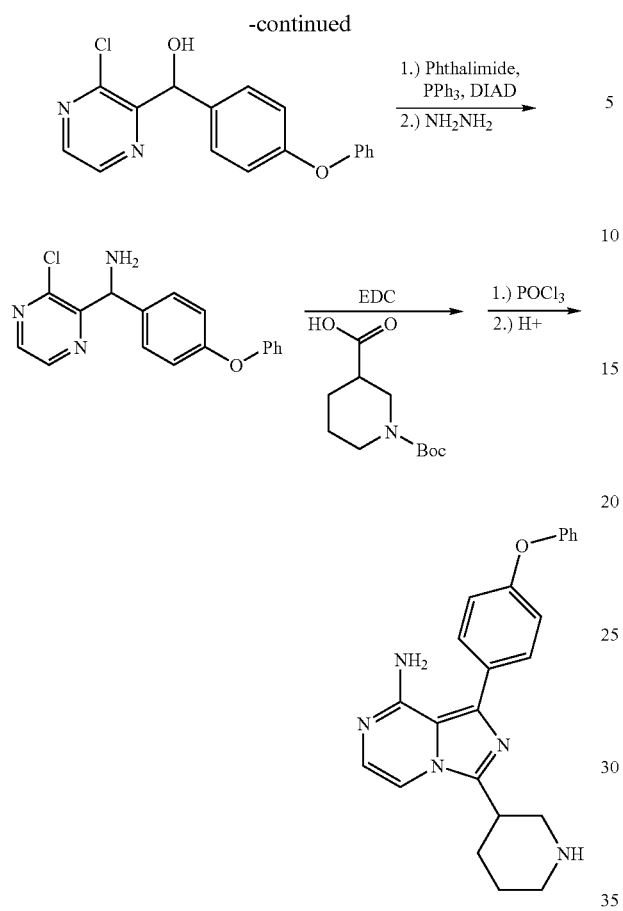
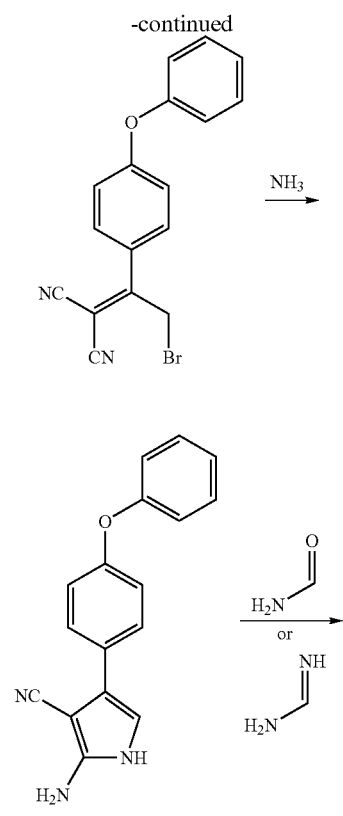
A non-limiting example of a synthetic approach towards the preparation of compounds containing the pyrrolopyrimidine moiety,
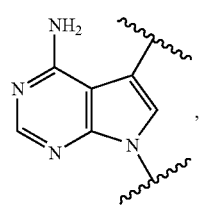
is shown in Scheme IV.
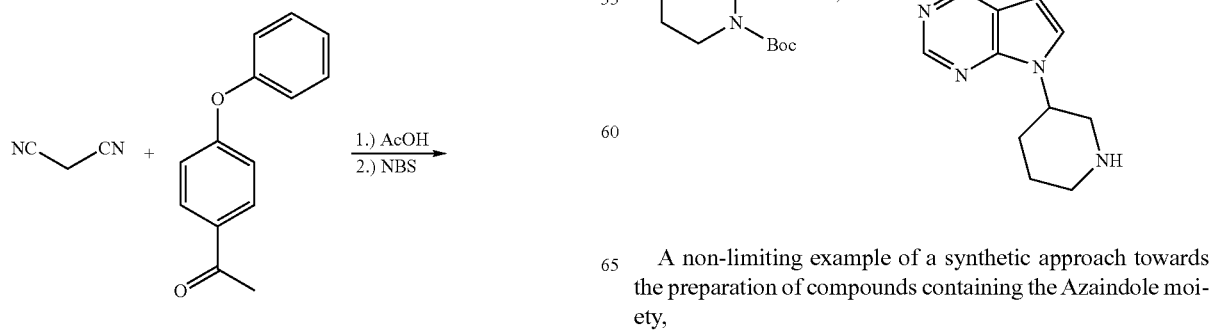
A non-limiting example of a synthetic approach towards the preparation of compounds containing the Azaindole moiety,

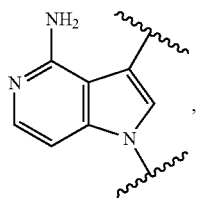

is shown in Scheme V.

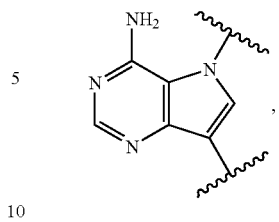

is shown in Scheme VI.

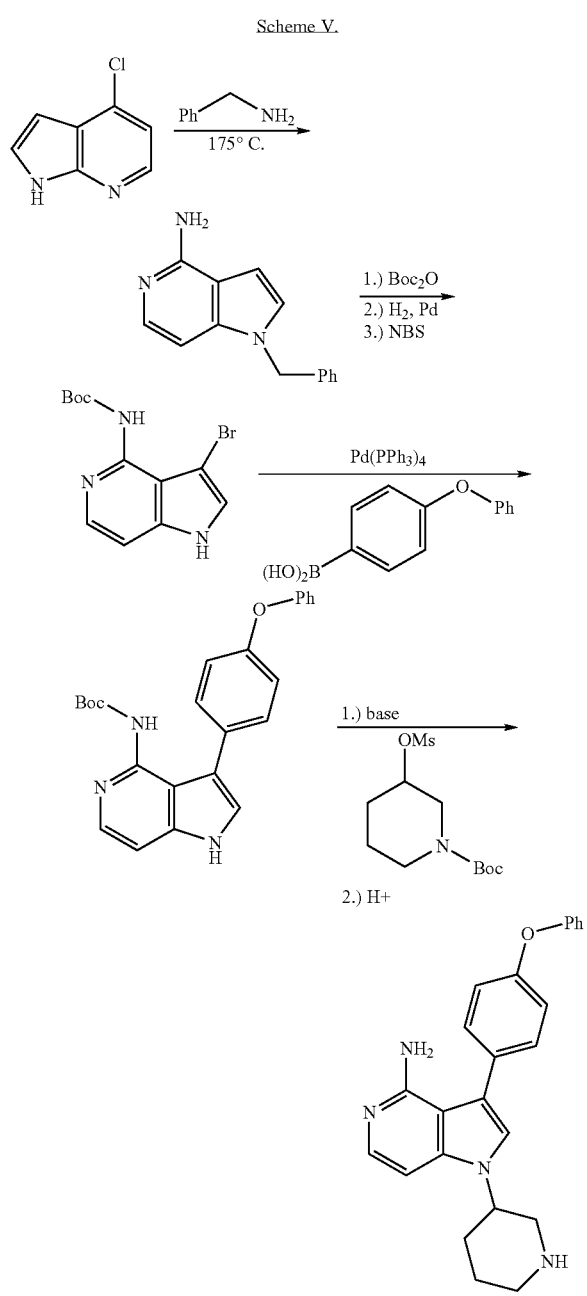

A non-limiting example of a synthetic approach towards the preparation of compounds containing the pyrrolopyrimidine moiety,

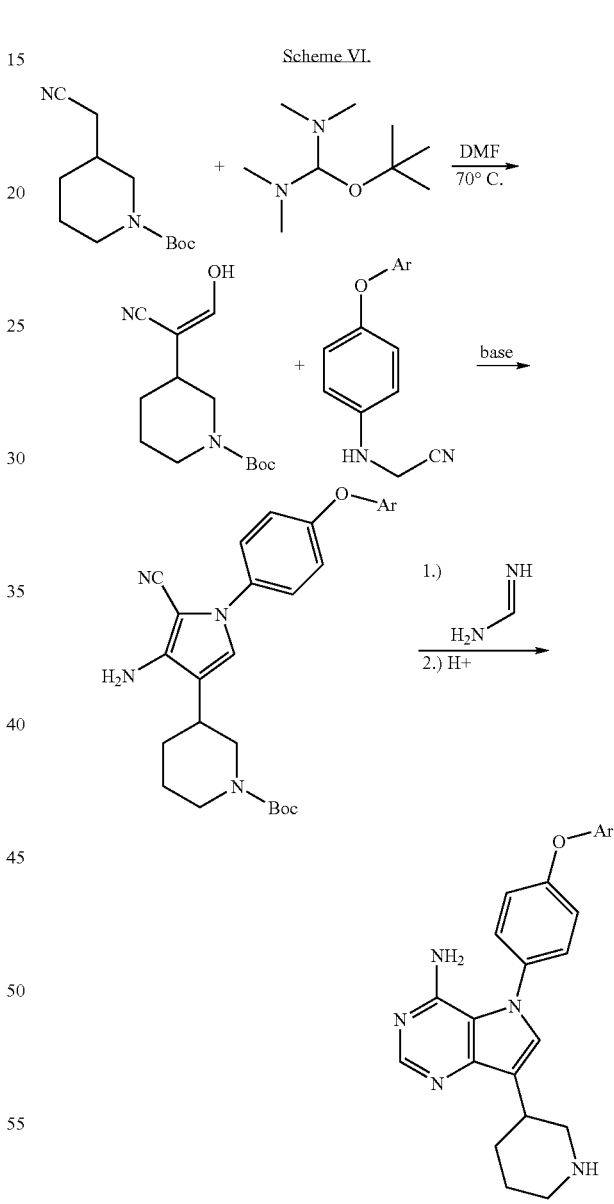

Using the synthetic methods described herein, tyrosine kinase inhibitors as disclosed herein are obtained in good yields and purity. The compounds prepared by the methods disclosed herein are purified by conventional means, such as, for example, filtration, recrystallization, chromatography, distillation, and combinations thereof.

Any combination of the groups described above for the various variables is contemplated herein.

Further Forms of Compounds

Compounds disclosed herein have a structure of any of Formula (A1-A6), Formula (B1-B6), Formula ($C_1$-$C_6$), or Formula (D1-D6). It is understood that when reference is made to compounds described herein, it is meant to include compounds of any of Formula (A1-A6), Formula (B1-B6), Formula (C1-C6), or Formula (D1-D6), as well as to all of the specific compounds that fall within the scope of these generic formulae, unless otherwise indicated. The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods such as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of any of Formula (A1-A6), Formula (B1-B6), Formula (C1-C6), or Formula (D1-D6) in unoxidized form can be prepared from N-oxides of compounds of any of Formula (A1-A6), Formula (B1-B6), Formula (C1-C6), or Formula (D1-D6) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is known, prodrugs of compounds can be designed (if desired) (for examples of this procedure applied to other compounds, see, e.g., Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the compounds herein described are prodrugs for another derivative or active compound.

Prodrugs are often useful because, in some situations, they are easier to administer than the parent drug. They are, for instance, bioavailable by oral administration whereas the parent is not. The prodrug optionally has improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated by reference for such disclosure.

Sites on the aromatic ring portion of compounds of any of Formula (A1-A6), Formula (B1-B6), Formula (C1-C6), or Formula (D1-D6) can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^3H$ and $^{14}C$ are incorporated, are useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Pharmaceutical Composition/Formulation

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and

*Pharmaceutical Dosage Forms and Drug Delivery Systems*, Seventh Ed. (Lippincott Williams & Wilkins 1999).

A pharmaceutical composition, as used herein, refers to a mixture of a compound described herein, such as, for example, compounds of any of Formula (A1-A6), Formula (B1-B6), Formula (C1-C6), or Formula (D1-D6), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any of Formula (A1-A6), Formula (B1-B6), Formula (C1-C6), or Formula (D1-D6), as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquioleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone®

XL-10), larch arabogalactan, Veegum®, polyethylene glycol, waxes, sodium alginate, and the like.

A "carrier" or "carrier materials" includes excipients in pharmaceutics and is selected on the basis of compatibility with compounds disclosed herein, such as, compounds of any of Formula (A1-A6), Formula (B1-B6), Formula (C1-C6), or Formula (D1-D6), and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator are also optionally used in the present compositions.

The term "diluent" refers to chemical compounds that are used to dilute the compound of interest prior to delivery. Diluents are be used to stabilize compounds because they can provide a more stable environment. Salts dissolved in buffered solutions (which also can provide pH control or maintenance) are optionally utilized as diluents, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per ml, dl, or l of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidine, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein are formulated for administration to a subject via, for example, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any of Formula (A1-A6), Formula (B1-B6), Formula (C1-C6), or Formula (D1-D6) can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of any of Formula (A1-A6), Formula (B1-B6), Formula (C1-C6), or Formula (D1-D6), with one or more pharmaceutical excipients to form a bulk blend composition. When referring to these bulk blend compositions as homogeneous, it is meant that the particles of the compound of any of Formula (A1-A6), Formula (B1-B6), Formula (C1-C6), or Formula (D1-D6), are dispersed evenly throughout the composition so that the composition is optionally readily subdivided into equally effective unit dosage forms, such as tablets, pills, and capsules. The individual unit dosages optionally also include film coatings, which disintegrate upon oral ingestion or upon contact with diluent.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of any of Formula (A1-A6), Formula (B1-B6), Formula (C1-C6), or Formula (D1-D6). In one embodiment, some or all of the particles of the compound of any of Formula (A1-A6), Formula (B1-B6), Formula (C1-C6), or Formula (D1-D6), are coated. In another embodiment, some or all of the particles of the compound of any of Formula (A1-A6), Formula (B1-B6), Formula (C1-C6), or Formula (D1-D6), are microencapsulated. In still another embodiment, the particles of the compound of any of Formula (A1-A6), Formula (B1-B6), Formula (C1-C6), or Formula (D1-D6), are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (A1-A6), Formula (B1-B6), Formula (C1-C6), or Formula (D1-D6), from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compound of any of Formula (A1-A6), Formula (B1-B6), Formula (C1-C6), or Formula (D1-D6), from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound of any of Formula (A1-A6), Formula (B1-B6), Formula (C1-C6), or Formula (D1-D6), described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula (A1-A6), Formula (B1-B6), Formula (C1-C6), or Formula (D1-D6), and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula (A1-A6), Formula (B1-B6), Formula (C1-C6), or Formula (D1-D6), which sufficiently isolate the compound of any of Formula (A1-A6), Formula (B1-B6), Formula (C1-C6), or Formula (D1-D6), from other non-compatible excipients. Materials compatible with compounds of any of Formula (A1-A6), Formula (B1-B6), Formula (C1-C6), or Formula (D1-D6), are those that delay the release of the compounds of any of Formula (A1-A6), Formula (B1-B6), Formula (C1-C6), or Formula (D1-D6), in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, OpadryYS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials. In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of Formula (A1-A6), Formula (B1-B6), Formula (C1-C6), or Formula (D1-D6), are formulated, for example, by methods such as spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media are optionally used. Furthermore, other methods such as roller compaction, extrusion/spheronization, coacervation, or nanoparticle coating are optionally used.

In one embodiment, the particles of compounds of any of Formula (A1-A6), Formula (B1-B6), Formula (C1-C6), or Formula (D1-D6), are microencapsulated prior to being formulated into one of the above forms. In still another embodiment, some or most of the particles are coated prior to being further formulated by using standard coating procedures, such as those described in *Remington's Pharmaceutical Sciences,* 20th Edition (2000).

In other embodiments, the solid dosage formulations of the compounds of any of Formula (A1-A6), Formula (B1-B6), Formula (C1-C6), or Formula (D1-D6), are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of Formula (A1-A6), Formula (B1-B6), Formula (C1-C6), or Formula (D1-D6), described herein, is formulated to include one or more pharmaceutical excipients and flavors. Such a powder is prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include compounds of Formula (A1-A6), are solid dispersions. Methods of producing such solid dispersions include, but are not limited to, for example, U.S. Pat. Nos. 4,343,789, 5,340,591, 5,456,923, 5,700,485, 5,723,269, and U.S. Pub. Appl 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

The pharmaceutical solid oral dosage forms including formulations described herein, which include a compound of any of Formula (A1-A6), Formula (B1-B6), Formula (C1-C6), or Formula (D1-D6), can be further formulated to provide a controlled release of the compounds Formula (A1-A6). Controlled release refers to the release of the compound of any of Formula (A1-A6), Formula (B1-B6), Formula (C1-C6), or Formula (D1-D6), from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form is optionally a compressed or molded or extruded tablet/mold (coated or uncoated) containing granules, powder, pellets, beads or particles of the active ingredient and/or other composition components, which are themselves coated or uncoated. The enteric coated oral dosage form is optionally a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers.

In some embodiments, the coating optionally, and usually does, contain a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) are optionally added to the coatings besides plasticizers to solubilize or disperse the coating material, and to improve coating performance and the coated product.

In other embodiments, the formulations described herein, which include compounds of Formula (A1-A6), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formula (A1-A6), Formula (B1-B6), Formula (C1-C6), or Formula (D1-D6), are administered, for example, using a variety of pulsatile formulations known in the including, but are not limited to, those described in U.S. Pat. Nos. 5,011,692, 5,017,381, 5,229,135, and 5,840,329. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284. In one embodiment, the controlled release dosage form is pulsatile release solid oral dosage form including at least two groups of particles, (i.e. multiparticulate) each containing the formulation described herein. The first group of particles provides a substantially immediate dose of the compound of any of Formula (A1-A6), Formula (B1-B6), Formula (C1-C6), or Formula (D1-D6), upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any of Formula (A1-A6), Formula (B1-B6), Formula (C1-C6), or Formula (D1-D6), in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any of Formula (A1-A6), Formula (B1-B6), Formula (C1-C6), or Formula (D1-D6).

Other types of controlled release systems suitable for use with the formulations described herein include, e.g., polymer-based systems, such as polylactic and polyglycolic acid, polyanhydrides and polycaprolactone; porous matrices, non-polymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, pharmaceutical formulations are provided that include particles of the compounds of any of Formula (A1-A6), Formula (B1-B6), Formula (C1-C6), or Formula (D1-D6), described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition to the particles of compounds of Formula (A1-A6), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogeneous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphatidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphatidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

Suitable intranasal formulations include, for example, U.S. Pat. Nos. 4,476,116, 5,116,817 and 6,391,452. Suitable intranasal formulations that include a compound of any of Formula (A1-A6), Formula (B1-B6), Formula ($C_1$-$C_6$), or Formula (D1-D6), are prepared, for example, as solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula (A1-A6), Formula (B1-B6), Formula (C1-C6), or Formula (D1-D6), described herein is in a form, for example, as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit is determined, for example, by providing a valve to deliver a metered amount. Capsules and cartridges of, such as, by way of example only, gelatin for use in an inhaler or insufflator is formulated containing a powder mix of the compound described herein and a suitable powder base such as lactose or starch.

Buccal formulations that include compounds of any of Formula (A1-A6), Formula (B1-B6), Formula ($C_1$-$C_6$), or Formula (D1-D6), is administered, for example, using a variety of formulations such as, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula (A1-A6), Formula (B1-B6), Formula (C1-C6), or Formula (D1-D6), is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compound of any of Formula (A1-A6), Formula (B1-B6), Formula (C1-C6), or Formula (D1-D6), and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions optionally take the form of tablets, lozenges, or gels.

Transdermal formulations described herein are administered, for example, using a variety of devices such as, but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

In one embodiment, the transdermal formulations described herein include at least three components: (1) a formulation of a compound of any of Formula (A1-A6), Formula (B1-B6), Formula (C1-C6), or Formula (D1-D6); (2) a penetration enhancer; and (3) an aqueous adjuvant. In addition, transdermal formulations optionally include additional components such as, gelling agents, creams and ointment bases, and the like. In some embodiments, the transdermal formulation further include a woven or non-woven backing material to enhance absorption and prevent the removal of the transdermal formulation from the skin. In other embodiments, the transdermal formulations described herein maintain a saturated or supersaturated state to promote diffusion into the skin.

Formulations suitable for transdermal administration of compounds described herein optionally employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein is optionally accomplished by means of iontophoretic patches and the like. Additionally, transdermal patches optionally provide controlled delivery of the compounds of any of Formula (A1-A6), Formula (B1-B6), Formula (C1-C6), or Formula (D1-D6). The rate of absorption is slowed, for example, by using rate-controlling membranes or by trapping the compound within a polymer matrix or gel. Conversely, absorption enhancers can be used to increase absorption. An absorption enhancer or carrier includes, for example, absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations that include a compound of any of Formula (A1-A6), Formula (B1-B6), Formula (C1-C6), or Formula (D1-D6), suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations may include aqueous or nonaqueous solutions, preferably with physiologically compatible buffers or excipients.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The compounds described herein can be used in the preparation of medicaments for the inhibition of Btk or a homolog thereof, or for the treatment of diseases or conditions that would benefit, at least in part, from inhibition of Btk or a homolog thereof. In addition, a method for treating any of the diseases or conditions described herein in a subject in need of such treatment, involves administration of pharmaceutical compositions containing at least one compound of any of Formula (A1-A6), Formula (B1-B6), Formula (C1-C6), or Formula (D1-D6), described herein, or a pharmaceutically acceptable salt, pharmaceutically acceptable N-oxide, pharmaceutically active metabolite, pharmaceutically acceptable prod rug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The irreversible Btk inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The initial administration is made, for example, according to established protocols, and then, based upon the observed effects, the dosage, modes of administration and times of administration are modified.

In certain instances, it may be appropriate to administer at least one irreversible Btk inhibitor compound described herein in combination with another therapeutic agent. By way of example only, if one of the side effects experienced by a patient upon receiving one of the irreversible Btk inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is based on an evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (A1-A6), (B1-B6), (C1-C6), or (D1-D6) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Exemplary Therapeutic Agents for Use in Combination with an Irreversible Btk Inhibitor Compound Where the subject is suffering from or at risk of suffering from an autoimmune disease, an inflammatory disease, or an allergy disease, an irreversible Btk inhibitor compound can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subjected can be treated with an irreversible Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with an irreversible Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with an irreversible Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride;

uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with an irreversible Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with an irreversible Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomustine, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with an irreversible Btk inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination an irreversible Btk inhibitor compound include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination with an irreversible Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with an irreversible Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323, 907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of Btk, or in which Btk is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever.

Example 1

Synthesis of Compounds

Preparation of 4-Amino-3-(4-phenoxyphenyl)-1H-pyrazolo[3,4-d]pyrimidine (Intermediate 2)

4-Amino-3-(4-phenoxyphenyl)-1H-pyrazolo[3,4-d]pyrimidine (Intermediate 2) is prepared as disclosed in International Patent Publication No. WO 01/019829. Briefly, 4-phenoxybenzoic acid (48 g) is added to thionyl chloride (100 mL) and heated under gentle reflux for 1 hour. Thionyl chloride is removed by distillation, the residual oil dissolved in toluene and volatile material removed at 80° C./20 mbar. The resulting acid chloride is dissolved in toluene (200 mL) and tetrahydrofuran (35 mL). Malononitrile (14.8 g) is added and the solution and stirred at −10° C. while adding diisopropylethylethylamine (57.9 g) in toluene (150 mL), while maintaining the temperature below 0° C. After 1 hour at 0° C., the mixture is stirred at 20° C. overnight. Amine hydrochloride is removed by filtration and the filtrate evaporated in vacuo. The residue is taken up in ethyl acetate and washed with 1.25 M sulphuric acid, then with brine and dried over sodium sulfate. Evaporation of the solvents gives a semisolid residue which is treated with a little ethyl acetate to give 4.1 g of 1,1-dicyano-2-hydroxy-2-(4-phenoxyphenyl)ethene as a white solid (m.p. 160-162° C.). The filtrate on evaporation gives 56.58 (96%) of 1,1-dicyano-2-hydroxy-2-(4-phenoxyphenyl)ethene as a grey-brown solid, which is sufficiently pure for further use.

1,1-Dicyano-2-hydroxy-2-(4-phenoxyphenyl)ethene (56.5 g) in acetonitrile (780 mL) and methanol (85 mL) is stirred under nitrogen at 0° C. while adding diisopropylethylamine (52.5 mL) followed by 2M trimethylsilyldiazomethane (150 mL) in THF. The reaction is stirred for 2 days at 20° C., and then 2 g of silica is added (for chromatography). The brown-red solution is evaporated in vacuo, the residue dissolved in ethyl acetate and washed well with water then brine, dried and evaporated. The residue is extracted with diethyl ether (3×250 mL), decanting from insoluble oil. Evaporation of the ether extracts gives 22.5 g of 1,1-dicyano-2-methoxy-2-(4-phenoxyphenyl)ethene as a pale orange solid. The insoluble oil is purified by flash chromatography to give 15.0 g of a red-orange oil. 1,1-Dicyano-2-methoxy-2-(4-phenoxyphenyl)ethene (22.5 g) and 1,1-dicyano-2-methoxy-2-(4-phenoxyphenyl)ethene oil (15 g) are treated with a solution of hydrazine hydrate (18 mL) in ethanol (25 mL) and heated on the steambath for 1 hour. Ethanol (15 mL) is added followed by water (10 mL). The precipitated solid is collected and washed with ethanol:water (4:1) and then dried in air to give 3-amino-4-cyano-5-(4-phenoxyphenyl)pyrazole as a pale orange solid.

3-Amino-4-cyano-5-(4-phenoxyphenyl)pyrazole (29.5 g) is suspended in formamide (300 mL) and heated under nitrogen at 180° C. for 4 hours. The reaction mixture is cooled to 30° C. and water (300 mL) is added. The solid is collected, washed well with water, then with methanol and dried in air to give of 4-amino-3-(4-phenoxyphenyl)-1H-pyrazolo[3,4-d]pyrimidine.

Example 1a

Synthesis of 1-(3-(4-amino-3-(4-phenoxyphenyl)-1H-pyrazolo[3,4-d]pyrimidin-1-yl)piperidin-1-yl)prop-2-en-1-one (Compound 4)

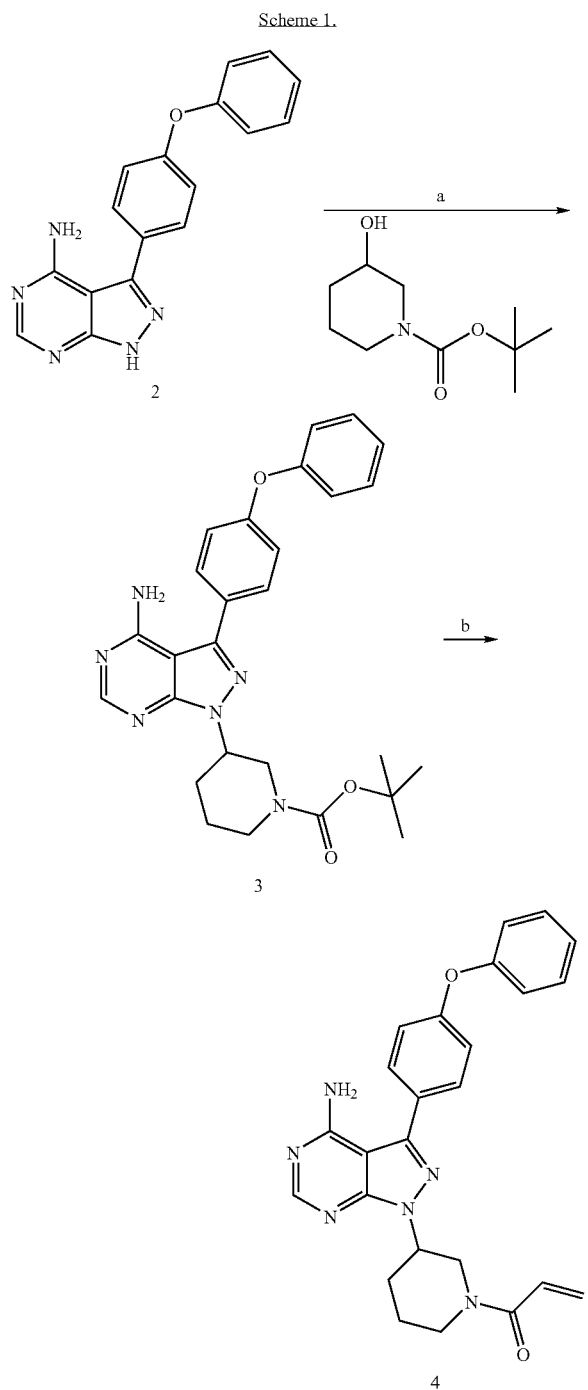

Synthesis of compound 4; a) polymer-bound triphenylphosphine (TPP), diisopropyl diazodicarboxylate (DIAD), tetrahydrofuran (THF); b) HCl/dioxane; then acryloyl chloride, triethylamine (TEA).

Compounds described herein were synthesized by following the steps outlined in Scheme 1. A detailed illustrative example of the reaction conditions shown in Scheme 1 is described for the synthesis of 1-(3-(4-amino-3-(4-phenoxyphenyl)-1H-pyrazolo[3,4-d]pyrimidin-1-yl)piperidin-1-yl)prop-2-en-1-one (Compound 4).

101 mg of 4-amino-3-(4-phenoxyphenyl)-1H-pyrazolo[3,4-d]pyrimidine and 330 mg of polymer-bound triphenylphosphine (TPP) (polymerlab) were mixed together with 5 mL of tetrahydrofuran (THF). tert-Butyl 3-hydroxypiperidine-1-carboxylate (200 mg; 2.0 equivalents) was added to the mixture followed by the addition of diisopropyl diazodicarboxylate (0.099 mL). The reaction mixture was stirred at room temperature overnight. The reaction mixture was filtered to remove the resins and the reaction mixture was concentrated and purified by flash chromatography (pentane/ethyl acetate=1/1) to give intermediate 3 (55 mg).

Intermediate 3 (48.3 mg) was treated with 1 mL of 4N HCl in dioxane for 1 hour and then concentrated to dryness. The residue was dissolved in dichloromethane and triethylamine (0.042 mL) was added followed by acryl chloride (0.010 mL). The reaction was stopped after 2 hours. The reaction mixture was washed with 5% by weight aqueous citric acid and then with brine. The organic layer was dried with $MgSO_4$, and concentrated. Flash chromatography (with $CH_2Cl_2$/MeOH=25/1) gave 22 mg of compound 4 as a white solid. MS (M+1): 441.2; $^1$H-NMR (400 MHz): 8.26, s, 1H, 7.65, m, 2H, 7.42, m, 2H, 7.1-7.2, m, 5H, 6.7-6.9, m, 1H, 6.1, m, 1H, 5.5-5.7, m, 1H, 4.7, m, 1H, 4.54, m, 0.5H, 4.2, m, 1H, 4.1, m, 0.5H, 3.7, m, 0.5H, 3.2, m, 1H, 3.0, m, 0.5H, 2.3, m, 1H, 2.1, m, 1H, 1.9, m, 1H, 1.6, m, 1H.

Example 1b

Synthesis of 1-((R)-3-(4-amino-3-(4-phenoxyphenyl)-1H-pyrazolo[3,4-d]pyrimidin-1-yl)piperidin-1-yl)prop-2-en-1-one (Compound 13)

The synthesis of compound 13 was accomplished using a procedure analogous to that described in Example 1a. EM (calc.): 440.2; MS (ESI) m/e (M+1H)$^+$: 441.1, (M−1H)$^-$: 439.2.

Example 1c

Synthesis of 1-((S)-3-(4-amino-3-(4-phenoxyphenyl)-1H-pyrazolo[3,4-d]pyrimidin-1-yl)piperidin-1-yl)prop-2-en-1-one (Compound 14)

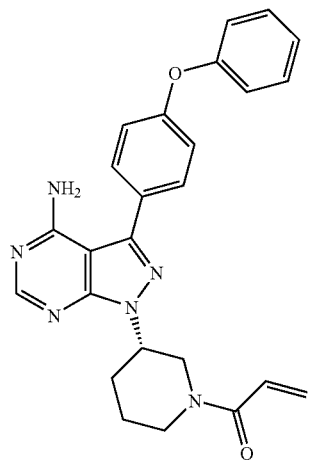

The synthesis of compound 14 was accomplished using a procedure analogous to that described for Example 1a. EM (calc.): 440.2; MS (ESI) m/e (M+1H)+: 441.5, (M−1H)−: 439.2.

Example 1d

Synthesis of 1-((S)-3-(4-amino-3-(4-phenoxyphenyl)-1H-pyrazolo[3,4-d]pyrimidin-1-yl)pyrrolidin-1-yl)prop-2-en-1-one (Compound 12)

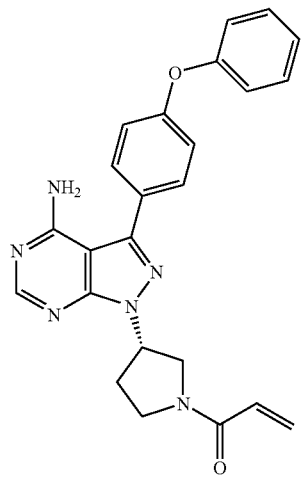

The synthesis of this compound was accomplished using a procedure analogous to that described for Example 1a. EM (calc.): 426.18; MS (ESI) m/e (M+1H)+: 427.2, (M−1H)−: 425.2.

Example 1e

Synthesis of 1-((R)-3-(4-amino-3-(4-phenoxyphenyl)-1H-pyrazolo[3,4-d]pyrimidin-1-yl)pyrrolidin-1-yl)prop-2-en-1-one (Compound 11)

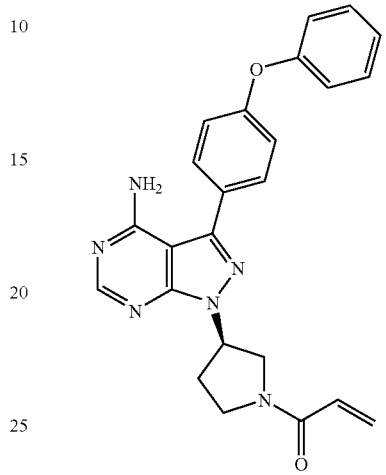

The synthesis of this compound was accomplished using a procedure analogous to that described for Example 1a. EM (calc.): 426.18; MS (ESI) m/e (M+1H)+: 427.2.

Example 1f

Synthesis of N-(1s,4s)-4-(4-amino-3-(4-phenoxyphenyl)-1H-pyrazolo[3,4-d]pyrimidin-1-yl)cyclohexyl)acrylamide (Compound 10)

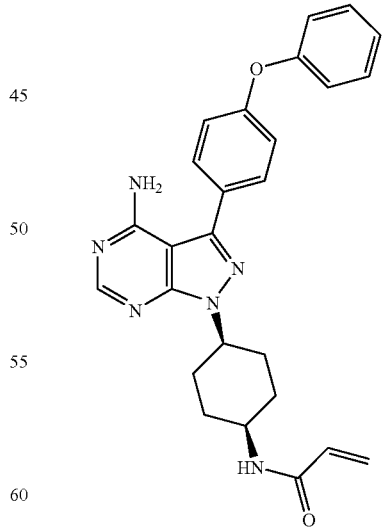

The synthesis of this compound was accomplished using a procedure analogous to that described for Example 1a. EM (calc.): 454.21; MS (ESI) m/e (M+1H)+: 455.1, (M−1H)−: 453.1.

Example 1g

Synthesis of 1-(3-(4-amino-3-(4-phenoxyphenyl)-1H-pyrazolo[3,4-d]pyrimidin-1-yl)piperidin-1-yl)sulfonylethene (Compound 6)

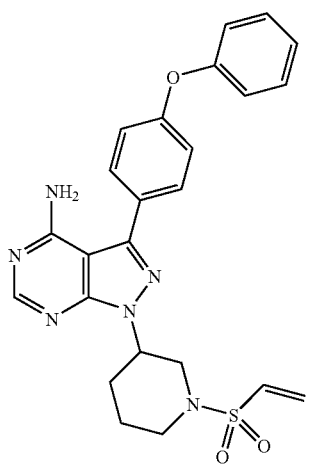

The synthesis of compound 6 was accomplished using a procedure analogous to that described for Example 1a. EM (calc.): 476.16; MS (ESI) m/e (M+1H)$^+$: 478.0, (M−1H)$^-$: 475.3.

Example 1h

Synthesis of 1-(3-(4-amino-3-(4-phenoxyphenyl)-1H-pyrazolo[3,4-d]pyrimidin-1-yl)piperidin-1-yl)prop-2-yn-1-one (Compound 8)

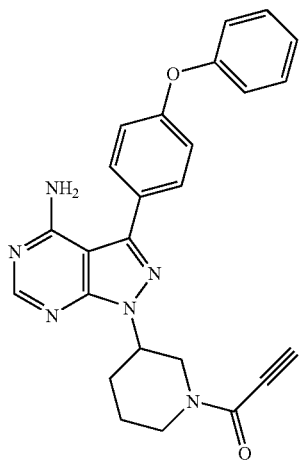

The synthesis of compound 8 was accomplished using a procedure analogous to that described for Example 1a. EM (calc.): 438.18; MS (ESI) m/e (M+1H)$^+$: 439.2, (M−1H)$^-$: 437.2.

Example 1i

Synthesis of (E)-1-(3-(4-amino-3-(4-phenoxyphenyl)-1H-pyrazolo[3,4-d]pyrimidin-1-yl)piperidin-1-yl)-4-(dimethylamino)but-2-en-1-one (Compound 15)

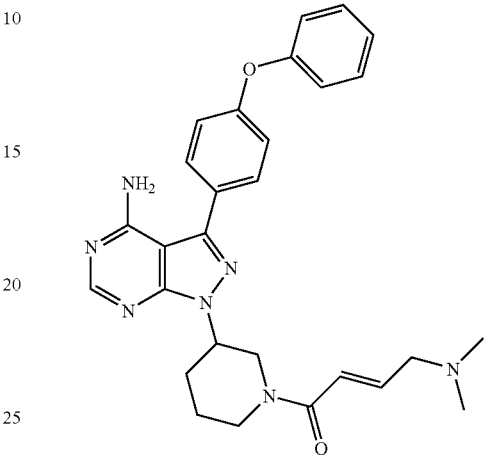

The synthesis of compound 15 was accomplished using a procedure analogous to that described for Example 1a. EM (calc.): 497.25; MS (ESI) m/e (M+1H)$^+$: 498.4, M−1H)$^-$: 496.

Example 2

Btk In Vitro Inhibitory Activity

The Btk IC$_{50}$s of compounds disclosed herein was determined in both an acellular kinase assay and in a cellular functional assay of BCR-induced calcium flux as described below.

Btk kinase activity was determined using a time-resolved fluorescence resonance energy transfer (TR-FRET) methodology. Measurements were performed in a reaction volume of 50 μL using 96-well assay plates. Kinase enzyme, inhibitor, ATP (at the K$_m$ for the kinase), and 1 μM peptide substrate (Biotin-AVLESEEELYSSARQ-NH$_2$) were incubated in a reaction buffer composed of 20 mM Tris, 50 mM NaCl, MgCl$_2$ (5-25 mM depending on the kinase), MnCl$_2$ (0-10 mM), 1 mM DTT, 0.1 mM EDTA, 0.01% bovine serum albumin, 0.005% Tween-20, and 10% DMSO at pH 7.4 for one hour. The reaction was quenched by the addition of 1.2 equivalents of EDTA (relative to divalent cation) in 25 μL of 1× Lance buffer (Perkin-Elmer). Streptavidin-APC (Perkin-Elmer) and Eu-labeled p-Tyr100 antibody (Perkin-Elmer) in 1× Lance buffer were added in a 25 μL volume to give final concentrations of 100 nM and 2.5 nM, respectively, and the mixture was allowed to incubate for one hour. The TR-FRET signal was measured on a multimode plate reader with an excitation wavelength ($\lambda_{Ex}$) of 330 nm and detection wavelengths ($\lambda_{Em}$) of 615 and 665 nm. Activity was determined by the ratio of the fluorescence at 665 nm to that at 615 nm. For each compound, enzyme activity was measured at various concentrations of compound. Negative control reactions were performed in the absence of inhibitor in replicates of six, and two no-enzyme controls were used to determine baseline fluorescence levels. Inhibition constants, K$_i$(app), were obtained using the program BatchK$_i$ (Kuzmic et al. (2000), Anal. Biochem. 286:45-50). IC$_{50}$s were obtained according to the equation:

$IC_{50} = \{Ki(app)/(1+[ATP]/K_m^{ATP})\} + [E]_{total}/2;$

For all kinases, $[ATP]=K_m^{ATP}$, $[Btk]_{total}=0.5$ nM and $[Lck]_{total}=6$ nM.

Calcium flux fluorescence-based assays were performed in a FlexStation II384 fluorometric imaging plate reader (Molecular Devices) according to manufacturer instructions. In brief, actively growing Ramos cells (ATCC) in RPM1 medium supplemented with 10% FBS (Invitrogen) were washed and re-plated in low serum medium at approximately $5 \times 10^5$ cells per 100 µl per well in a 96-well plate. Compounds to be assayed were dissolved in DMSO and then diluted in low serum medium to final concentrations ranging from 0 to 10 µM (at a dilution factor of 0.3). The diluted compounds were then added to each well (final DMSO concentration was 0.01%) and incubated at 37 degree in 5% $CO_2$ incubator for one hour. Afterwards, 100 µl of a calcium-sensitive dye (from the Calcium 3 assay kit, Molecular Devices) was added to each well and incubated for an additional hour. The compound-treated cells were stimulated with a goat anti-human IgM antibody (80 ug/ml; Jackson ImmunoResearch) and read in the FlexStation II384 using a $\lambda_{Ex}=485$ nm and $\lambda_{Em}=538$ nm for 200 seconds. The relative fluorescence unit (RFU) and the IC$_{50}$ were recorded and analyzed using a built-in SoftMax program (Molecular devices).

TABLE 2

Assay data for representative compounds

| Compound No. | R | Btk IC$_{50}$ (nM) | Ramos Cell Ca Flux IC$_{50}$ (nM) |
|---|---|---|---|
| 4 | (3-piperidinyl)-N-acryloyl | 0.72 | 10 |
| 5 | (3-piperidinyl)-N-crotonoyl | 20 | 89 |
| 6 | (3-piperidinyl)-N-vinylsulfonyl | 0.52 | 92 |
| 7 | (3-piperidinyl)-N-chloroacetyl | 0.58 | 9 |

TABLE 2-continued
Assay data for representative compounds
| Compound No. | R | Btk IC$_{50}$ (nM) | Ramos Cell Ca Flux IC$_{50}$ (nM) |
|---|---|---|---|
| 8 | 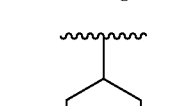 | 0.72 | 9 |
| 9 | 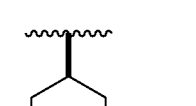 | 3.6 | 48 |
| 10 | 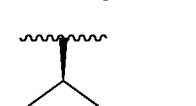 | 0.58 | 3 |
| 11 | 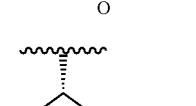 | 1.6 | 24 |
| 12 | | 1.9 | 90 |

TABLE 2-continued

Assay data for representative compounds

| Compound No. | R | Btk IC$_{50}$ (nM) | Ramos Cell Ca Flux IC$_{50}$ (nM) |
|---|---|---|---|
| 13 | (R)-3-piperidinyl-N-acryloyl | <0.5 | 10 |
| 14 | (S)-3-piperidinyl-N-acryloyl | 1.4 | 7 |
| 15 | 3-piperidinyl-N-(4-dimethylamino-but-2-enoyl) | 2.5 | 36 |

Two lines of evidence demonstrated irreversible inhibition of Btk by these compounds. First, after recombinant Btk was pretreated with compounds, its activity was not recovered by repeat washing with inhibitor-free medium (see, e.g., J. B. Smaill, et al., *J. Med. Chem.* 1999, 42, 1803). Second, a major mass peak was observed by mass spectrometry corresponding to the molecular weight of a 1:1 covalent complex between compound 4 and Btk (Compound 4: 440 Da, recombinant Btk kinase domain: 33,487 Da; Complex: expected 33,927 Da, observed 33,927 Da).

These compounds are highly potent inhibitors of Btk kinase activity with IC$_{50}$s in the sub-nanomolar to single digit nanomolar range for in vitro kinase activity. Their IC$_{50}$s in the (Ramos cell) Ca$^{2+}$ flux assay ranged from 3 to 92 nM.

Of note, we found that three types of Michael acceptors, acrylamide, vinyl sulfonamide and propargylamide, exhibited strong interactions with Btk. Adding a trans-oriented methyl group to the vinyl group decreased potency as shown by compound 5, which was 28-fold less potent than 4. This presumably relates to the reduced electrophilicity of the more substituted olefin. Compound 15 with a tertiary amine group gained back some potency compared to 5, even though it still suffered a potency drop relative to compound 13. Compound 10 was about 6-fold more potent than 9, presumably due to the difference in the electrophile orientation. Finally, R configuration was determined as the slightly preferred absolute stereochemistry configuration by two sets of enantiomers (11 vs. 12 and 13 vs. 14).

Example 3

Inhibition of Btk

We further characterized the properties of these compounds by assaying a number of cellular biochemical and functional endpoints. In particular, we sought to assess the selectivity of these compounds for inhibition of Btk versus the closely related protein kinases Lck, Lyn, and Syk. In anti-IgM-stimulated Ramos cells (a human B cell line), we assayed Btk-dependent phosphorylation of PLC-γ1; Lyn and Syk-dependent phosphorylation of tyrosine 551 on Btk; and BCR-activated calcium flux. We also measured the effect of compound 4 on Jurkat cells, a human T cell line in which Lck and Itk, but not Btk are required for T cell receptor mediated $Ca^{2+}$ flux. As shown in Table 3, compound 4 exhibited significant selectivity for Btk in cellular assays. In anti-IgM stimulated Ramos cells, compound 4 inhibited the phosphorylation of PLC-γ1 with an $IC_{50}$=0.014 μM, while the Lyn and Syk-dependent phosphorylation of tyrosine 551 on Btk was inhibited more weakly ($IC_{50}$>7.5 μM). Thus, compound 4 exhibits a >500-fold selectivity between Btk and Lyn or Syk in cells. Further, compound 4 was 11-fold less active in inhibiting $Ca^{2+}$ flux than in Ramos cells, supporting the expected selectivity for B versus T cells.

TABLE 3

Cellular assay data for compound 4

| Cmpd | $Btk^a$ (nM) | $Lck^a$ (nM) | $Lyn^a$ (nM) | Btk $p551^b$ (μM) | $pPLC-γ1^b$ (μM) | Ramos Ca Flux$^b$ (μM) | Jurkat Ca Flux$^b$ (μM) |
|---|---|---|---|---|---|---|---|
| 4 | $0.72^b$ | 97 | 14 | >7.5 | 0.014 | 0.0405 | 0.466 |

$^a$Ki (app)
$^b$IC$_{50}$

Example 4

Use of Compound 4 to Treat Rheumatoid Arthritis

The in vivo efficacy of compound 4 was evaluated in a mouse model of rheumatoid arthritis. Arthritis was induced in Balb/c mice by administration of anti-collagen antibodies and lipopolysaccharide (LPS). See Nandakumar et al. (2003), Am. J. Pathol. 163:1827-1837.

Female Balb/c mice were treated with 100 mg/kg of Chemicon mAb cocktail to Type II collagen intravenously on Day 0 and 1.25 mg/kg of LPS intraperitoneally on Day 1. Compound 4 was administered orally in a methylcellulose-based aqueous suspension formulation at 1, 3, 10 and 30 mg/kg once daily starting on Day 2 through Day 12. Blood samples were collected at 0.5 and 2 hours post dose of compound 4 administration on Day 12 (see Table 4). The serum concentrations of compound 4 were quantified by LC/MS/MS. Twenty four hours post dose, levels of compound 4 were below the level of quantitation.

TABLE 4

Dose and Time Dependence of Compound 4 Concentration in Plasma

| Dose (mg/kg/day) | Collection Time (h) | Conc (μM) Mean | SD |
|---|---|---|---|
| 1 | 0.5 | 0.0657 | 0.0153 |
|  | 2 | 0.0485 | 0.0200 |
| 3 | 0.5 | 0.250 | 0.019 |
|  | 2 | 0.135 | 0.059 |
| 10 | 0.5 | 0.635 | 0.053 |
|  | 2 | 0.670 | 0.190 |
| 30 | 0.5 | 1.72 | 0.15 |
|  | 2 | 1.10 | 0.19 |

Inhibition of arthritis by compound 4 was dose-dependent, with a maximum effect (>95% inhibition) at dose levels of 10 and 30 mg/kg. The plasma concentrations of compound 4 that induced this maximum effect were in the 0.6-1.7 μM range at $T_{max}$ (2 hr) and did not need to be sustained at high levels for 24 hours to achieve efficacy, which is not surprising for an irreversible inhibitor. Based on sequence analysis and molecular modeling, the irreversible inhibitors described herein are proposed to form a covalent bond with Cys 481 of Btk (e.g., the Michael reaction acceptor portion of the compounds described herein react with the Cys 481 residue of Btk). Based on sequence homology analysis (FIG. 1), the compounds presented herein are also expected to act as irreversible inhibitors of kinases having a Cys 481 or a homologous cysteine residue, but to bind reversibly with kinases having a different amino acid at the 481 position within a catalytic domain sequence that is otherwise homologous to that of Btk. See, e.g., the sequences listed in FIG. 1. See also the sequence alignments of tyrosine kinases (TK) published on the world wide web at kinase.com/human/kinome/phylogeny.html.

Example 5

Inhibition of a Panel of Kinases for Compound 4 and Compound 10

TABLE 5

| V | Cys | Compound 4 IC50 (nM) | Compound 10 IC50 (nM) |
|---|---|---|---|
| EGFR | Y | 0.52 | 20.60 |
| BTK | Y | 0.53 | 0.96 |
| JAK3 | Y | 10.36 | 8278.00 |
| Bmx/ETK | Y | 0.76 | 1.13 |
| BLK | Y | 0.52 | 0.17 |
| ITK | Y | 11.70 | 909.90 |
| LCK | N | 1.98 | 1.03 |
| SYK | N | >10,000 | >10,000 |

Example 6

Degree of Cytoxicity for Compound 4 and Compound 10

TABLE 6

| Cell line | Origin | PCI-32765 GI50 (uM) | PCI-31883 GI50 (uM) |
|---|---|---|---|
| DHL-6 | Lymphoma | 0.75 | 0.009 |
| DOHH2 | Lymphoma | 0.77 | 0.011 |
| DLCL2 | Lymphoma | 1.3 | 4.82 |
| Mino | Lymphoma | 1.9 | 0.12 |
| Raji | Lymphoma | >10 | >10 |
| CRL-8062 | Myeloma | >10 | >10 |
| A549 | Lung | >10 | 3.13 |
| NCI-H460 | Lung | >10 | >10 |
| BT-549 | Breast | >10 | 2.79 |
| SK-BR3 | Breast | 0.44 | 0.24 |
| MDA-MB-361 | Breast | >10 | >10 |
| MDA-MB-468 | Breast | >10 | >10 |
| MDA-MB-231 | Breast | >10 | >10 |
| MDA-MB-453 | Breast | <0.001 | 0.54 |

Example 7

Inhibition of Mast Cell Degranulation

Human CD34+ cells differentiated to mast cells by 9 weeks in culture in the presence of 1 ng/ml IL-3, 50 ng/ml IL-6, 100 ng/ml SCF. Cells were incubated with IgE+IL-4 for 4 days and then degranulation was induced by cross-linking with anti-IgE. Degranulation quantitated using hexosaminidase assay. Compound did not inhibit degranulation induced by the Ca++ ionophore ionomycin and did not affect cell viability as determined by Alamar Blue assay. Compound 4 has an IC50 in MC degranulation less than 100 nanomolar. As such, compounds described herein are used for the treatment of inflammatory diseases, such as asthma.

Example 8

Pharmaceutical Compositions

The compositions described below are presented with a compound of Formula (A1-A6) for illustrative purposes; any of the compounds of any of Formulas (A1-A6), (B1-B6), (C1-C6), or (D1-D6) are optionally used in such pharmaceutical compositions.

Example 8a

Parenteral Composition

To prepare a parenteral pharmaceutical composition suitable for administration by injection, 100 mg of a water-soluble salt of a compound of Formula (A1-A6) is dissolved in DMSO and then mixed with 10 mL of 0.9% sterile saline. The mixture is incorporated into a dosage unit form suitable for administration by injection.

Example 8b

Oral Composition

To prepare a pharmaceutical composition for oral delivery, 100 mg of a compound of Formula (A1-A6) is mixed with 750 mg of starch. The mixture is incorporated into an oral dosage unit for, such as a hard gelatin capsule, which is suitable for oral administration.

Example 8c

Sublingual (Hard Lozenge) Composition

To prepare a pharmaceutical composition for buccal delivery, such as a hard lozenge, mix 100 mg of a compound of Formula (A1-A6), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 8d

Inhalation Composition

To prepare a pharmaceutical composition for inhalation delivery, 20 mg of a compound of Formula (A1-A6) is mixed with 50 mg of anhydrous citric acid and 100 mL of 0.9% sodium chloride solution. The mixture is incorporated into an inhalation delivery unit, such as a nebulizer, which is suitable for inhalation administration.

Example 8e

Rectal Gel Composition

To prepare a pharmaceutical composition for rectal delivery, 100 mg of a compound of Formula (A1-A6) is mixed with 2.5 g of methylcelluose (1500 mPa), 100 mg of methylparaben, 5 g of glycerin and 100 mL of purified water. The resulting gel mixture is then incorporated into rectal delivery units, such as syringes, which are suitable for rectal administration.

Example 8f

Topical Gel Composition

To prepare a pharmaceutical topical gel composition, 100 mg of a compound of Formula (A1-A6) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 8g

Ophthalmic Solution Composition

To prepare a pharmaceutical ophthalmic solution composition, 100 mg of a compound of Formula (A1-A6) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 9

Levels of Tonic BCR Signaling Predict Response to Compound 4

To identify biomarkers that correlate with response to Compound 4, phosphorylation events in the BCR signal transduction pathway were investigated. A panel of phospho-specific antibodies that recognize activating phosphorylation sites on Syk, Btk, BLNK, PLC-g1, PLC-g2, ERK, and AKT were used and tested the effects of Compound 4 on both basal phosphorylation and phosphorylation following BCR stimulation driven by anti-IgM or anti-IgG cross-linking. We examined phosphorylation patterns in both a Compound 4 sensitive cell line (DOHH2) and a Compound 4 resistant cell line (Ramos).

Compound 4 inhibits most BCR-stimulus induced phosphorylation events with similar potency in both cell lines. However, when we examined basal phosphorylation levels, we found higher basal phosphorylation in DOHH2 compared to Ramos, with phospho-ERK in particular indicating higher levels of basal or tonic signaling in DOHH2. Furthermore, Compound 4 significantly decreased pERK levels in unstimulated DOHH2 cells (IC50<10 nM), but not in Ramos cells.

A panel of nine Btk expressing B cell lymphoma cell lines was screened for basal pERK levels. Seven lines expressed significantly higher levels of basal pERK, and of these, 5 were sensitive to Compound 4 (GI50<1.3 uM), while the two cell lines with low pERK levels were resistant to Compound 4. This data shows that tonic BCR signaling contributes to the survival of a subset of lymphoma cell lines, and that inhibition of this signaling by Compound 4 is correlated with induction of apoptosis.

Two additional experiments demonstrate that sensitivity to Compound 4 is correlated with high levels of lines pERK. First 1 uM of Compound 4 reduces expression of the known ERK transcriptional target Egr-1 within 1 hr, with maximal downregulation (10-fold) achieved by 4 hr. Second, in the lymphoma cell line WSU-DLCL2, BCR cross-linking by anti-IgG (30 ug/ml) overcome inhibition of pERK by Compound 4, showing that strong BCR stimulus activates parallel pathways to pERK that do not require Btk. BCR stimulus also rescues WSU-DLCL2 from Compound 4 induced cytotoxicity, further confirming that inhibition of pERK is correlated with apoptosis induction by Compound 4. Taken together these data show high levels of pERK or ERK transcriptional targets such as Egr-1 serve as useful markers for lymphomas in which tonic BCR signaling is contributing to cell survival and that these lymphomas are particularly sensitive to BCR pathway inhibitors such as Compound 4.

What is claimed is:

1. A compound having the structure of Formula (D5):

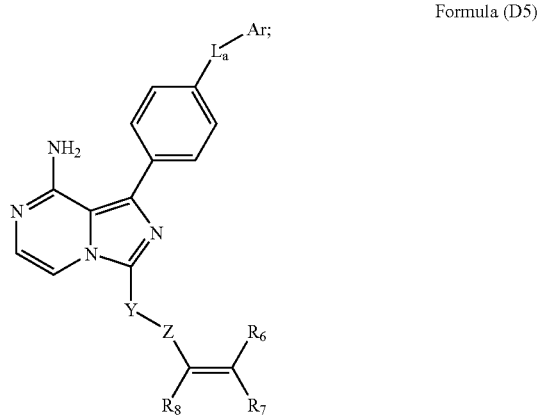

Formula (D5)

wherein:
- La is $CH_2$, O, NH or S;
- Ar is a substituted or unsubstituted aryl;
- Y is a 4-, 5-, 6-, or 7-membered cycloalkyl ring, or
- Y is a 4-, 5-, 6-, or 7-membered monocyclic nitrogen-containing heterocycloalkyl ring;
- Z is C(=O), OC(=O), NHC(=O), S(=O)$_x$, or NHS(=O)$_x$, where x is 1 or 2;
- $R_8$ is H;
- $R_7$ is H, unsubstituted $C_1$-$C_4$alkyl, $C_1$-$C_6$alkoxyalkyl, $C_1$-$C_8$alkylaminoalkyl, or $C_1$-$C_4$alkyl(phenyl); or
- $R_7$ and $R_8$ taken together form a bond;
- $R_6$ is H, unsubstituted $C_1$-$C_4$alkyl, $C_1$-$C_6$alkoxyalkyl, $C_1$-$C_8$alkylaminoalkyl, or $C_1$-$C_4$alkyl(phenyl); or a pharmaceutically acceptable salt thereof.

2. The compound of claim 1 wherein La is O.

3. The compound of claim 2 wherein Z is C(=O), NHC(=O), or S(=O)$_2$.

4. The compound of claim 3 wherein each of $R_7$ and $R_8$ is H or $R_7$ and $R_8$ taken together form a bond.

5. The compound of claim 3 wherein $R_6$ and $R_8$ are each H.

6. The compound of claim 1 wherein Y is a 5-membered monocyclic nitrogen-containing heterocycloalkyl ring.

7. The compound of claim 1 wherein Y is a 6-membered monocyclic nitrogen-containing heterocycloalkyl ring.

8. The compound of claim 1 wherein Ar is an unsubstituted phenyl.

9. A pharmaceutical composition comprising a compound of claim 1 and a pharmaceutically acceptable excipient.

10. The compound of claim 1, having the structure of:

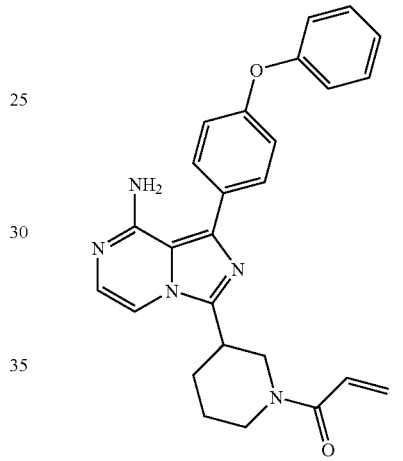

11. A pharmaceutical composition comprising a compound of claim 10 and a pharmaceutically acceptable excipient.

* * * * *

UNITED STATES PATENT AND TRADEMARK OFFICE
CERTIFICATE OF CORRECTION

PATENT NO. : 7,825,118 B2
APPLICATION NO. : 11/964285
DATED : November 2, 2010
INVENTOR(S) : Lee Honigberg et al.

It is certified that error appears in the above-identified patent and that said Letters Patent is hereby corrected as shown below:

In the Specification

Column 8, line 21: delete "Graves' disease Sjögren's syndrome" and replace with --Graves' disease, Sjögren's syndrome--

Column 9, line 25: delete "Graves' disease Sjögren's syndrome" and replace with --Graves' disease, Sjögren's syndrome--

Column 10, line 42: delete "forms a covalent bound with the activated form" and replace with --forms a covalent bond with the activated form--; line 53: delete "forms a covalent bound with the activated form" and replace with --forms a covalent bond with the activated form--; line 64: delete "forms a covalent bound with the activated form" and replace with --forms a covalent bond with the activated form--

Column 11, line 7: delete "forms a covalent bound with the activated form" and replace with --forms a covalent bond with the activated form--; line 18: delete "forms a covalent bound with the activated form" and replace with --forms a covalent bond with the activated form--

Column 28, line 6: delete "This enantiomer of compound 4 completed inhibited the development of arthritis" and replace with --This enantiomer of compound 4 completely inhibited the development of arthritis--; line 39: delete "Graves' disease Sjögren's syndrome" and replace with --Graves' disease, Sjögren's syndrome--

Signed and Sealed this
Nineteenth Day of August, 2014

Michelle K. Lee
*Deputy Director of the United States Patent and Trademark Office*

CERTIFICATE OF CORRECTION (continued)
U.S. Pat. No. 7,825,118 B2

Column 33, lines 59-60: delete "$R_9$ and $R_{10}$ can together form a 5-, 6-, 7-, or 8-membered heterocyclic ring" and replace with --$R_{11}$ and $R_{10}$ can together form a 5-, 6-, 7-, or 8-membered heterocyclic ring--

Column 55, between lines 47 and 65: delete the following structure:

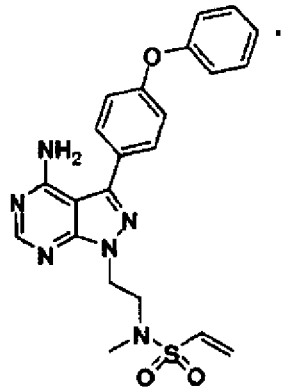 " and replace with the following structure: -- 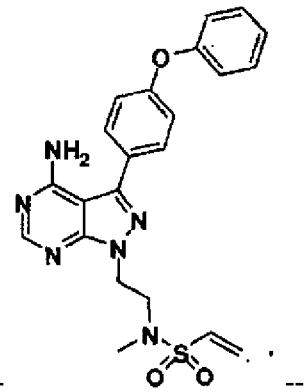 --

Column 58, between lines 1 and 22: delete the following structure:

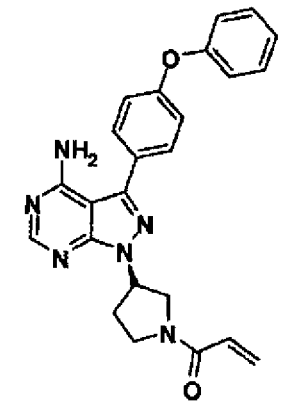 " and replace with the following structure: -- 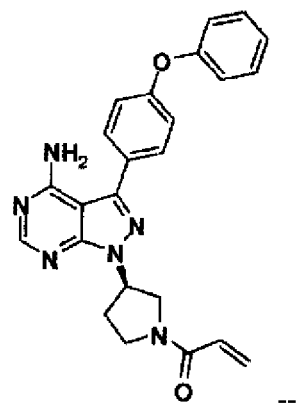 --

Column 58, between lines 26 and 45: delete the following structure:

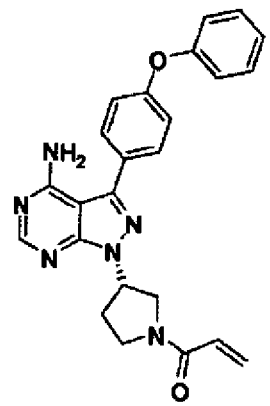 " and replace with the following structure: -- 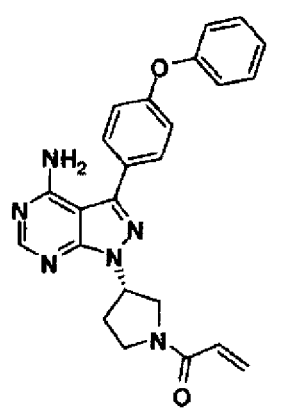 --

CERTIFICATE OF CORRECTION (continued)
U.S. Pat. No. 7,825,118 B2

Column 58, between lines 49 and 65: delete the following structure:

" 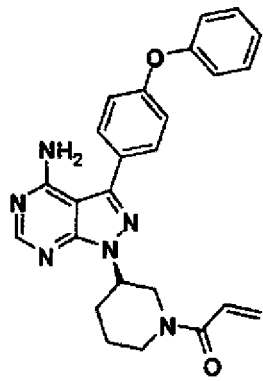 " and replace with the following structure: -- 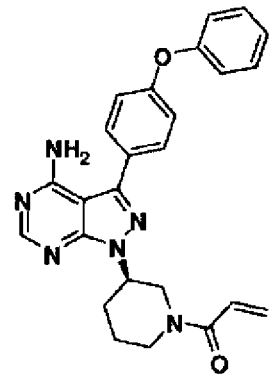 --

Column 59, between lines 1 and 17: delete the following structure:

" 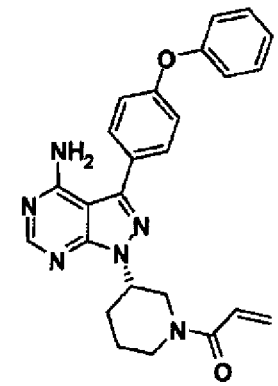 " and replace with the following structure: -- 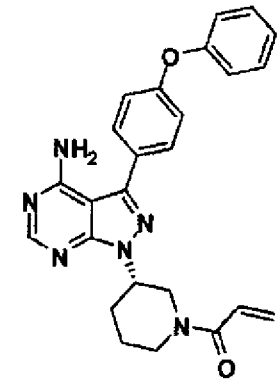 --

Column 59, between lines 20 and 36: delete the following structure:

" 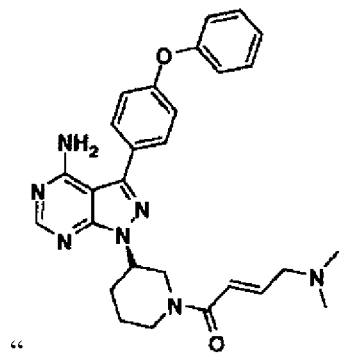 " and replace with the following structure: -- 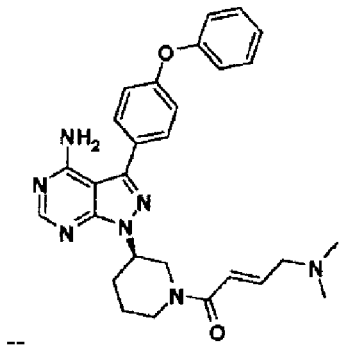 --

CERTIFICATE OF CORRECTION (continued)
U.S. Pat. No. 7,825,118 B2

Column 117, between lines 38 and 45: delete the following structure for compound 15:

" 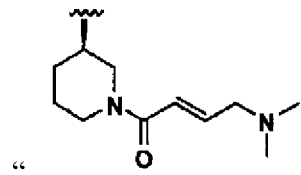 " and replace with the following structure: -- 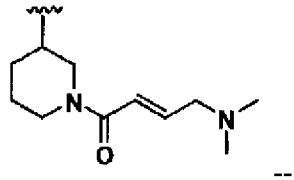 --